US011560543B2

(12) United States Patent
Bucci et al.

(10) Patent No.: US 11,560,543 B2
(45) Date of Patent: Jan. 24, 2023

(54) GENETICALLY ENGINEERED MICROORGANISMS AND METHODS OF USE

(71) Applicant: University of Massachusetts, Boston, MA (US)

(72) Inventors: Vanni Bucci, Brookline, MA (US); Jacob Palmer, Oxford (GB); Christopher Brigham, Waban, MA (US); Mark Silby, Bridgewater, MA (US)

(73) Assignee: University of Massachusetts, Boston, MA (US)

( * ) Notice: Subject to any disclaimer, the term of this patent is extended or adjusted under 35 U.S.C. 154(b) by 408 days.

(21) Appl. No.: 16/647,269

(22) PCT Filed: Sep. 14, 2018

(86) PCT No.: PCT/US2018/051079
§ 371 (c)(1),
(2) Date: Mar. 13, 2020

(87) PCT Pub. No.: WO2019/055781
PCT Pub. Date: Mar. 21, 2019

(65) Prior Publication Data
US 2020/0270569 A1 Aug. 27, 2020

Related U.S. Application Data

(60) Provisional application No. 62/558,725, filed on Sep. 14, 2017.

(51) Int. Cl.
C12N 15/09 (2006.01)
C12N 1/20 (2006.01)
(Continued)

(52) U.S. Cl.
CPC ............... C12N 1/20 (2013.01); A61K 35/74 (2013.01); C12N 15/70 (2013.01); C12N 2510/00 (2013.01); C12N 2800/10 (2013.01)

(58) Field of Classification Search
CPC ...................................................... C12N 15/09
See application file for complete search history.

(56) References Cited

U.S. PATENT DOCUMENTS

| 2006/0269988 A1 | 11/2006 | Royer et al. |
| 2015/0209393 A1 | 7/2015 | Wook et al. |
| 2022/0218787 A1 | 7/2022 | Bucci et al. |

FOREIGN PATENT DOCUMENTS

| WO | WO 2010/025267 | 3/2010 |
| WO | WO 2016/072936 | 5/2016 |

(Continued)

OTHER PUBLICATIONS

Fomenko et al., "Regulation of microcin C51 operon expression: the role of global regulators of transcription," Res Microbiol 152: 469-479, 2001.*

(Continued)

Primary Examiner — Rosanne Kosson
(74) Attorney, Agent, or Firm — Fish & Richardson P.C.

(57) ABSTRACT

This disclosure relates to genetically engineered microorganisms for treating or reducing the risk of bacterial infections or dysbiosis, and further discloses methods of making and using such microorganisms.

30 Claims, 13 Drawing Sheets
Specification includes a Sequence Listing.

(51) Int. Cl.
*A61K 35/74* (2015.01)
*C12N 15/70* (2006.01)

(56) References Cited

FOREIGN PATENT DOCUMENTS

| WO | WO 2016/210373 A2 | 12/2016 |
|----|-------------------|---------|
| WO | WO 2018/237198    | 12/2018 |
| WO | WO 2019/055781    | 3/2019  |

OTHER PUBLICATIONS

Mercado et al., "The production in vivo of microcin E492 with antibacterial activity depends on salmochelin and EntF," Journal of Bacteriology, AUg. 1, 2008, 190(15):5464-71.

Nolan et al., "Biosynthetic tailoring of microcin E492m: post-translational modification affords an antibacterial siderophore—peptide conjudate," Journal of the American Chemical Society, Nov. 21, 2007, 129(46):14336-47.

PCT International Preliminary Report on Patentability in International Appln. No. PCT/US2018/051079, dated Mar. 17, 2020, 9 pages.

PCT International Preliminary Report on Patentability in International Appln. No. PCT/US2020/031182, dated Nov. 2, 2021, 6 pages.

PCT International Preliminary Report on Patentability in International Appl. No. PCT/US2021/019225, dated Feb. 3, 2022, 11 pages.

PCT International Search Report and Written Opinion in International Appln. No. PCT/US2021/019225, dated Aug. 10, 2021, 11 pages.

Azpiroz et al.. "Microcin H47 system: an *Escherichia coli* small genomic island with novel features." PLoS One, Oct. 11, 2011, 6(10):e26179, 7 pages.

Azpiroz et al., "Microcins and urovinilence in *Escherichia coli*. Microbial pathogenesis," Nov. 2009, 47(5):274-80.

Bayro et al., "Structure of antibacterial peptide microcin J25: a 21-residue lariat protoknot," Journal of the American Chemical Society, Oct. 13. 2003. 125(41):12382-3.

Bucci et al., "The evolution of bacteriocin production in bacterial biofilms," The American Naturalist, Dec. 1, 2011, 178(6):E162-73.

Chatham-Stephens et al., "Emergence of extensively drug-resistant *Salmonella typhi* infections among travelers to or from Pakistan—United States, 2016-2018." Morbidity and Mortality Weekly Report. Jan. 11, 2019, 68(1):11. 5 pages.

Daefiler et al., "Engineering bacterial thiosulfate and tetrathionate sensors for detecting gut inflammation," Molecular Systems Biology, Apr. 2017, 13(4):923, 13 pages.

David et al., "Epidemic of carbapenem-resistant Klebsiella pneumoniae in Europe is driven by nosocomial spread," Nature Microbiology. Nov. 2019, 4(11): 1919-29.

Delgado et al., "YojI of *Escherichia coli* functions as a microcin J25 efflux pump." Journal of Bacteriology, May 15, 2005, 187(10):3465-70.

EP European Search Report in European Appln. No. 18856596.4, dated Aug. 7, 2020, 17 pages.

Geldart et al., "pMPES: a modular peptide expression system for the delivery of antimicrobial peptides to the site of gastrointestinal infections using probiotics," Pharmaceuticals, Dec. 2016, 9(4):60, 16 pages.

Gibson et al., "Enzymatic assembly of DNA molecules up to several hundred kilobases," Nature Methods, May 2009, 6(5):343-5.

Landry et al., "Engineering diagnostic and therapeutic gut bacteria." Microbiology Spectrum, Oct. 2017, 5(5), 22 pages.

Medina et al., "Tackling threats and future problems of multidnig-resistant bacteria," How To Overcome the Antibiotic Crisis, 2016, 3-33.

Metelev et al., "Structure of microcin B-like compounds produced bv Pseudomonas svringae and species specificity of their antibacterial action," Journal of Bacteriology, Sep. 15, 2013, 195(18):4129-37.

Nadell et al., "Cutting through the complexity of cell collectives. Proceedings of the Royal Society B: Biological Sciences." Mar. 22, 2013, 280, 11 pages.

Ng et al., "Microbiota-liberated host sugars facilitate post-antibiotic expansion of enteric pathogens," Nature, Oct. 2013, 502(7469):96-9.

Nolan et al., "Investigations of the MceIJ-catalvzed post-translational modification of the microcin E492 C-terminus: linkage of ribosomal and nonribosomal peptides to form "trojan horse" antibiotics." Biochemistry, Sep. 2, 2008, 47(35):9289-99.

Palmer et al.. "Engineered probiotic for the inhibition of *Salmonella* via tetrathionate-induced production of microcin H47." ACS Infectious Diseases, Jan. 12. 2018. 4(1):39-45.

PCT International Search Report and Written Opinion in International Appln. No. PCT/US2020/031182, dated Aug. 18, 2020, 9 pages.

Poey et al., "Comparative analysis of chromosome-encoded microcins," Antimicrobial Agents and Chemotherapy, Apr. 1, 2006, 50(4):1411-8.

Riglar et al., "Engineered bacteria can function in the mammalian gut long-term as live diagnostics of inflammation." Nature Biotechnology, Jul. 2017, 35(7):653-8.

Vassiliadis et al.. "Siderophore microcins form the first family of structure-related antimicrobial peptides from Enterobacteriaceae: isolation and characterization of microcins M and H47," Antimicrob Agents Chemother, Jan. 2010, 54:288-97.

EP Extended European Search Report in European Appln, No. 18856596.4, dated Nov. 10, 2020, 15 pages.

Duquesne et al., "Microcins, gene-encoded antibacterial peptides from enterobacteria," Natural Product Reports, 2007, 24(4):708-34.

EP European Search Report in European Appln. No. 20802507.2, dated Jun. 15, 2022, 9 pages.

Geldart et al., "pMPES: a modular peptide expression system for the delivery of antimicrobial peptides to the site of gastrointestinal infections using probiotics," Pharmaceuticals, Oct. 2, 2016, 9(4):60, 16 pages.

Mortzfeld et al., "MccI47 selectively inhibits enteric bacteria and reduces carbapenem-resistant Klebsiella pneumoniae colonization in vivo when administered via an engineered live biotherapeutic," bioRxiv, Jan. 1, 2021, vol. 2021, 22 pages.

Poey et al., "Virulence profiles in uropathogenic *Escherichia coli* isolated from pregnant women and children with urinary tract abnormalities," Microbial Pathogenesis, May 1, 2012, 52(5):292-301.

Vassiliadis et al., "Isolation and characterization of two members of the siderophore-microcin family, microcins M and H47," Antimicrobial Agents and Chemotherapy, Jan. 2010, 54(1):288-97.

Rodriguez, E. et al. The Structural Gene for Microcin H47 Encodes a Peptide Precursor with Antibiotic Activity. Antimicrobial Agents and Chemotherapy. Sep. 1999. pp. 2179-2182; Figure 1A; Table 1; abstract; p. 2176, second col. fifth paragraph; p. 2179, first col. third paragraph; p. 2180, first col. fourth paragraph; p. 2180, second col. second paragraph.

Patzer, S. et al. The collcin G, H and X determinants encode microclns M-^ind H47, which might utilize the catecholate siderophore receptors FepA, Cir, Flu and IroN. Microbiology. 2003, vol. 149, pp. 2557-2570, DOI 10.1099/mlc.0.26396-0; Figure 1; Table 1; abstract; p. 2557, first col. first paragraph-second col. second paragraph.

Sassone-Corsi, M. et al. Microclns Mediate Competition Among Enterobacteriaceae In the Inflamed Gut Name; Dec. 8, 2016; vol. 540, pp. 1-25 (Author's Manuscript), dol:10.1038/nature20557; entire document.

SearchReport and Written Opinion for PCT/US18/51079 dated Feb. 7, 2019, 13 pages.

\* cited by examiner

GENETICALLY ENGINEERED MICROORGANISMS AND METHODS OF USE

This application is a U.S. National Stage Application under 35 USC § 371 of International Patent Application Serial No. PCT/US2018/051079, filed on Sep. 14, 2018, entitled "GENETICALLY ENGINEERED MICROORGANISMS AND METHODS OF USE," which claims the benefit of U.S. Provisional Patent Application Ser. No. 62/558,725, filed on Sep. 14, 2017, entitled "GENETICALLY ENGINEERED MICROORGANISMS AND METHODS OF USE." The entire contents of the foregoing applications are hereby incorporated by reference.

STATEMENT OF FEDERALLY SPONSORED RESEARCH

This invention was made with government support under Grant No. AI112985 awarded by National Institute of Allergy and Infectious Disease, Grant No. 1458347 awarded by National Science Foundation, and Grant No. DK056754 awarded by the National Institutes of Health. The Government has certain rights in the invention.

TECHNICAL FIELD

This disclosure relates to genetically engineered microorganisms and methods of use.

BACKGROUND

The CDC estimates that every year, more than 2 million people acquire multi-drug-resistant infections, resulting in over 23,000 related deaths (Antibiotic Resistance Threats in the United States, 2013|Antibiotic/Antimicrobial Resistance CDC.). Medical complications related to the emergence of antibiotic-resistant bacteria is a major issue in modern healthcare due to the resulting increase in morbidity, mortality, length of hospitalization, and related healthcare costs (Medina and Pieper (2016) Tackling Threats and Future Problems of Multidrug-Resistant Bacteria, in How to Overcome the Antibiotic Crisis. Stadler and Dersch, Eds., pp 3-33. Springer International Publishing). *Enterobacteriaceae* spp. are among the leading causes of morbidity and mortality worldwide and include opportunistic pathogens Carbapenem-resistant *Klebsiella* spp., Fluoroquinolone-resistant *Salmonella* spp., adherent-invasive *Escherichia coli* (Ng et al., (2013) Microbiota-liberated host sugars facilitate post-antibiotic expansion of enteric pathogens, Nature 502, 96-99.); (Winter et al., (2013) Host-derived nitrate boosts growth of *E. coli* in the inflamed gut, Science 339, 708-711.). According to the CDC, drug-resistant *Salmonella* spp. are responsible for more than 100,000 infections, while their non-resistant counterparts already account for 1.2 million infections and 450 deaths in the US every year (Antibiotic Resistance Threats in the United States, 2013|Antibiotic/Antimicrobial Resistance|CDC.). Thus, there is pressing need to develop novel therapeutics that selectively kill pathogenic bacteria, reduce infection rates (and duration of infection), and curb the emergence of new drug-resistance mechanisms.

SUMMARY

This disclosure relates to genetically engineered microorganisms that do not exist in nature and methods of use of such microorganisms to treat bacterial infection or dysbiosis. In one aspect, this disclosure provides an engineered strain of *E. coli* capable of using an environmental signal indicative of intestinal inflammation as an inducing agent, resulting in production of small antimicrobial peptides such as microcin, that are capable of inhibiting the organism responsible for the inflammation.

In one aspect, the disclosure relates to genetically engineered microorganisms, wherein the microorganism includes a microcin operon, and a controllable promoter for the microcin operon. In some embodiments, the microcin operon comprises, consists of, or consists essentially of one or more microcin genes, and the controllable promoter controls a level of expression of the one or more microcin genes, thereby controlling the amount of microcin produced by the genetically engineered microorganism, and wherein either or both of the microcin operon and the controllable promoter are heterologous to the microorganism.

In some embodiments, the genetically engineered microorganism is a bacterium. In some embodiments, the genetically engineered microorganism is *Escherichia coli*. In some embodiments, the *E. coli* is *E. coli* Nissle 1917 (EcN) or *E. coli* NGF-19.

In some embodiments, the microcin operon includes one or more Microcin H47 (MccH47) genes.

In some embodiments, the microcin operon comprises, consists of, or consists essentially of mchB, mchC, and mchD. In some embodiments, the microcin operon comprises, consists of, or consists essentially of mchB, mchC, mchD, mchE, mchF, mchX and mchI. In certain embodiments, the microorganism comprises mchA. In some embodiments, the microcin operon comprises, consists of, or consists essentially of Microcin M genes or Microcin J25 genes. In some embodiments, the controllable promoter is a pBAD promoter, or a Pttr promoter. In certain embodiments, the microorganism further includes ttrBCA operon.

In some embodiments, the microcin operon and the controllable promoter are in the genome of the microorganism. In some embodiments, the microcin operon and the controllable promoter are in a vector.

In another aspect, this disclosure relates to vectors comprising, consisting of, or consisting essentially of a set of microcin genes, and a controllable promoter, wherein the controllable promoter is capable of controlling the expression level of at least one microcin gene. In some embodiments, the set of microcin genes comprises, consists of, or consists essentially of one or more Microcin H47 (MccH47) genes. In some embodiments, the set of microcin genes comprises, consists of, or consists essentially of mchA, mchB, mchC, and mchD. In some embodiments, the set of microcin genes comprises, consists of, or consists essentially of mchA, mchB, mchC, mchD, mchE, mchF, mchX and mchI. In some embodiments, the set of microcin genes comprises, consists of, or consists essentially of Microcin M genes or Microcin J25 genes.

In some embodiments, the controllable promoter is a pBAD promoter, or a Pttr promoter, or the J23119 promoter. In certain embodiments, the vector further includes ttrBCA operon. In some embodiments, the vector is a plasmid.

In another aspect, the disclosure relates to vectors comprising, consisting of, or consisting essentially of (1) mchA; (2) an operon comprising, consisting of, or consisting essentially of mchB, mchC, mchD, mchE, mchF; and (3) a controllable promoter, wherein the controllable promoter controls the expression level of the operon.

In some embodiments, the operon further includes mchX and mchI. In certain embodiments, the controllable promoter is a pBAD promoter, or a Pttr promoter. In some embodiments, the operon further includes ttrB, ttrC, and ttrA. In various embodiments, the vector further includes ttrS and ttrR. In some embodiments, the vector is a plasmid.

In another aspect, the disclosure relates to vectors comprising, consisting of, or consisting essentially of (1) an operon comprising mchA, mchS1, and mchS4; (2) a controllable promoter, wherein the controllable promoter controls the expression level of the operon detailed in (1); (3) an operon comprising, consisting of, or consisting essentially of mchX, mchI, mchB, mchC, mchD, mchE, mchF; and (4) a controllable promoter, wherein the controllable promoter controls the expression level of the operon detailed in (3).

In some embodiments, the controllable promoter is a pBAD promoter, or the J23119 promoter. In certain embodiments, the vector is a plasmid.

In another aspect, the disclosure relates to compositions for treating a bacterial infection, wherein the compositions include the genetically engineered microorganism. In some embodiments, the composition is packaged in a capsule for intestinal delivery. In certain embodiments, the bacterial infection is a gram-negative bacterial infection. In some embodiments, the bacterial infection is carbapenem-resistant enterobacteriaceae infection, *Campylobacter* infection, *E. coli* infection, *Salmonella* infection, *Shigella* infection and/or *Yersinia* infection.

In another aspect, the disclosure relates to methods of treating intestinal dysbiosis. The methods include the steps of identifying a subject as having intestinal dysbiosis; and administering to the subject a therapeutically effective amount of a composition including the genetically engineered microorganism.

In some embodiments, the subject is a human and the composition is administered by endoscopy, enteroscopy, colonoscopy, a nasoduodenal catheter, enema, or by oral administration. In certain embodiments, the composition is orally administered, e.g., in a capsule.

In another aspect, the disclosure also relates to methods of treating a bacterial infection. The methods include the steps of identifying a subject as having a bacterial infection; and administering to the subject a therapeutically effective amount of a composition including the genetically engineered microorganism. In some embodiments, the subject is a human and the composition is administered by endoscopy, enteroscopy, colonoscopy, a nasoduodenal catheter, enema, or by oral administration.

In some embodiments, the composition is orally administered, e.g., in a capsule. In certain embodiments, the bacterial infection is a gram-negative bacterial infection. In some embodiments, the bacterial infection is carbapenem-resistant enterobacteriaceae infection, *Campylobacter* infection, *E. coli* infection, *Salmonella* infection, *Shigella* infection and/or *Yersinia* infection.

In another aspect, the disclosure relates to methods of reducing a risk of a bacterial infection. The methods include the steps of identifying a subject as having a risk of a bacterial infection; and administering to the subject a composition including the genetically engineered microorganism. In some embodiments, the subject is being administered one or more antibiotics. In some embodiments, the subject is a human and the composition is administered by endoscopy, enteroscopy, colonoscopy, a nasoduodenal catheter, enema, or by oral administration. In certain embodiments, the composition is orally administered, e.g., in a capsule.

The use of bacterial-derived microcins for the treatment of enterobacterial colitis is a novel and potent alternative to antibiotics. This disclosure provides genetically engineered *E. coli* that produce microcin, an anti-microbial peptide that inhibits growth of *S. Typhimurium*. In some embodiments, the genetically engineered *E. coli* produces microcin dependent on extracellular L-rhamnose. In some embodiments, the genetically engineered *E. coli* produces microcin dependent on extracellular tetrathionate, a molecule that is known to increase in concentration during *Salmonella* intestinal infection. As described below, in vitro assays demonstrated that the genetically engineered *E. coli* not only prevents *S. Typhimurium* growth in static agar inhibition assays, but also significantly reduces *S. Typhimurium* fitness in pairwise ecological competition experiments. Thus, one advantage of this genetically engineered living therapeutic is that the genetically engineered microorganism can induce a specific microbiome correction during the course, or at the onset of, a particular disease state.

As used herein, the term "operon" refers to a functioning unit of DNA sequence containing a set of genes, wherein the set of genes is under the control of a promoter.

As used herein, the term "promoter" refers to a DNA sequences that initiates transcription.

As used herein, the term "microcin operon" refers to an operon comprising at least one microcin gene.

As used herein, the terms "genetically engineered" or "genetically engineering" refer to altering the genetic material (DNA or RNA) existed in a natural microorganism, or introducing exogenous genetic material into a natural microorganism.

As used herein, the term "genetically engineered microorganism" refers to a microorganism that has at least one genetic alteration not normally found in a naturally occurring strain of the referenced microorganism species, including wild-type strains of the referenced species. The term "wild-type" refers to the common genotype or phenotype, or genotypes or phenotypes, of a microorganism as it is found in nature. Genetic alterations include, for example, a gene deletion or some other functional disruption of the genetic material. Genetic alterations also include modifications that introduce expressible nucleic acids encoding metabolic polypeptides, other nucleic acid additions, nucleic acid deletions and/or other functional disruption of the genetic material in the microorganism. Such modification can be made, for example, in coding regions and functional fragments thereof, for heterologous, homologous or both heterologous and homologous polypeptides for the referenced species. Genetically engineered microorganisms are often derived from wild-type microorganisms by making one or more genetic modifications to the wild-type microorganism.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application

DETAILED DESCRIPTION

Figure 1B:
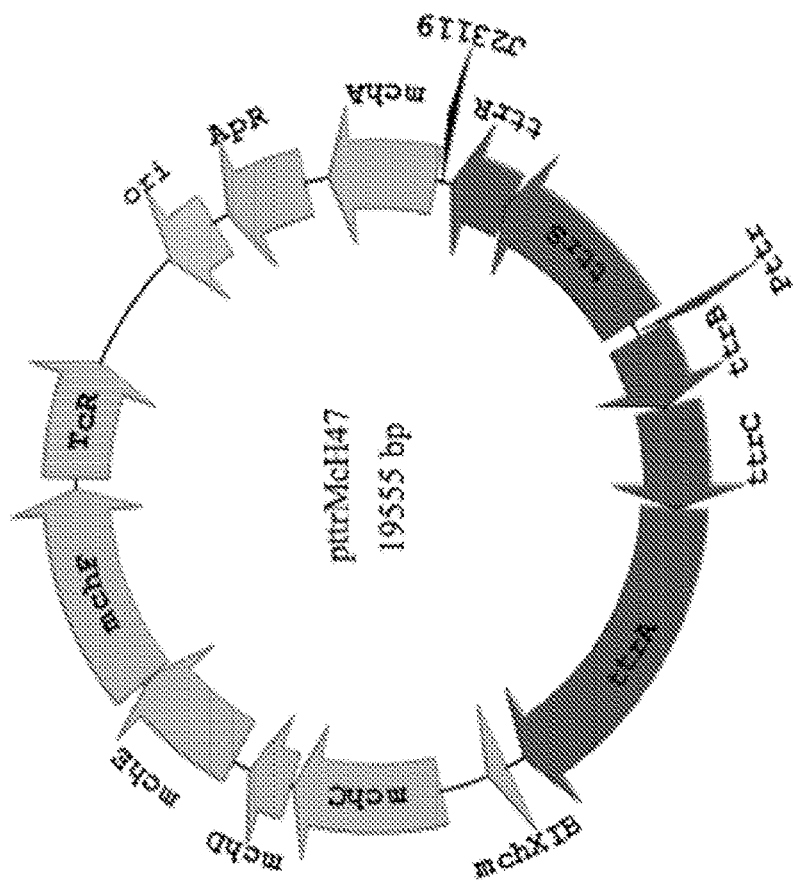
FIG. 1B is a plasmid map for pttrMcH47 that enables tetrathionate-induced production of MccH47.

Members of drug-resistant Enterobacteriaceae spp. include opportunistic pathogens (e.g., Salmonella spp.) are among the leading causes of morbidity and mortality worldwide. Overgrowth of these bacteria is considered a hallmark of intestinal dysbiosis. Some gut commensals produce microcins, small antimicrobial peptides, that inhibit growth of select pathogens. As described herein, select gut commensals can be genetically altered and used to effectively treat pathogenic bacteria infections and/or to limit the growth of pathogenic bacteria.

This disclosure provides genetically engineered probiotics developed to inhibit Salmonella spp. upon exposure to tetrathionate, a molecule produced in the inflamed gut during the course of Salmonella infection. The disclosure provides plasmid-based systems capable of producing microcin H47 in response to extracellular tetrathionate. Escherichia coli transformed with the aforementioned plasmid systems inhibit growth of Salmonella dependent on extracellular tetrathionate. In direct competition assays between the engineered E. coli and Salmonella, the engineered E. coli had a considerable increase in fitness advantage in the presence of 1 mM tetrathionate as compared to when grown in the absence of tetrathionate. This disclosure demonstrates that that microcin H47 (MccH47), a post-translationally modified peptide, originally isolated from E. coli strain H47, can inhibit Salmonella growth in vitro.

Additionally, this disclosure provides genetically engineered probiotics capable of conditionally producing MccH47, including those that produce MccH47 dependent on extracellular L-rhamnose and those that produce MccH47 dependent on extracellular tetrathionate.

Microcins

Microcins are low-molecular-weight antimicrobial peptides secreted by members of the Enterobacteriaceae family. They include, e.g., Class I microcins, Class IIa microcins, Class IIb microcins, and Class IIc microcins. Class I microcins have molecular masses <5 kDa, are post-translationally modified, and bind to a spectrum of targets.

Class IIa microcins . . . [add details]

Class IIb microcins are relatively large (~5-10 kDa) polypeptides and feature a C-terminal siderophore post-translational modification. Class IIb microcins include, e.g., Microcin H47 (MccH47), MccE492, MccM, MccG492 and MccI47.

Class IIc microcins . . . [add details]

MccH47

Microcin H47 (MccH47) is a bactericidal antibiotic. Due to its size, it shares with other microcins the ability to pass through cellophane membranes. MccH47 has been shown to be active to inhibit various bacteria, e.g., gram-negative bacteria, *E. coli, Salmonella, Enterobacter, Shigella, Klebsiella*, and *Proteus* spp. The genes required for production of MccH47 are clustered in a 10-kb DNA segment located in the *E. coli* chromosome and include the genes: mchA, mchB, mchC, mchD, mchE, mchF, mchI, mchX, mchS1, and mchS4. Four genes, mchA, mchB, mchC, and mchD, are devoted to MccH47 synthesis; an immunity gene, mchI, encoding a small, 69-residue integral membrane peptide; and two further genes, mchE and mchF, are required for the secretion of the antibiotic into the extracellular medium.

A small gene, mchX, was found upstream of the immunity determinant; preliminary results point to its involvement in the activation of its own expression and probably in that of downstream immunity and production genes. The mchX, mchI, and mchB genes are located in the central region of the MccH47 genetic system, and are often referred as mchXIB. They are known to be transcribed in the same direction, towards mchB. Notably, the mchX gene may be involved in the activation of its own expression and the activation of downstream immunity and production genes.

MccH47 production is a process involving three main steps: synthesis of the precursor peptide MchB, subsequent maturation of the molecule, and its final secretion. These MccH47 genes are described, e.g., in Vassiliadis et al. (2010) Isolation and characterization of two members of the siderophore-microcin family, microcins M and H47, Antimicrobial agents and chemotherapy 54.1:288-297, which is incorporated herein by reference in its entirety. MccH47 production is a process involving three main steps: synthesis of the precursor peptide MchB, subsequent maturation and post-translational modification of the molecule, and secretion of the molecule. The complexity of the MccH47 antibiotic system parallels that of other microcin systems, such as those of microcins B17 and C7. MccH47 maturation, in which mchA, mchC, and mchD gene products are known to be necessary, is believed to endow the antibiotic molecule with the ability to enter cells.

mchA gene sequence (SEQ ID NO: 1)

```
ATGCGAAAACGTATTCTTTTTATTGGCCCACCGCTGTACGGTTTGTTATACCCATTGATT

TCTCTGGCTCAGGCCTTTCGTGTAATCGGACATGATGTAGTA

ATTAGTAGTGCTGGCAAATTCGCGAATAAAGCAGCAGAAGCTGGACTGGT

TGTTTTTGATGCAGTTCCAGGTTTAGATTCAGAGGCTGGATATCGCCATCA

GGAAGAGTTGAGGAAAAAAAGTAATATTATTGGTCATTTCTCTTTTTTTAG

CGATGAAATGGCAGATAACCTCATCGATTTTGCAGGAAAATGGAGGCCAG

ATTTAATAGTCTATCCCCCGCTTGGTCCGGCAGGCCCATTGGTTGCTGCTA

AATATAGAATTCCTTCAGTGATGCTGGCTGTTGGATTCGCGCATACATCTG

CCCATATTCAGATGTTAAACCGTTCTTTAAGCAATGCTTACAGGCGGCATG

GAGTCAGCGGTCCACTATGTGATTTAGCATGGATTGATGTTGCTCCCCCAA

GTATGAGCATTCTTAAAAATGCTGAAGAACCGGTTATCTCAATGAGATAT

ATTCCTTATAACGGAGGTGCTGTAAAGGAAACATGGTGGGACAGGGATTC

TGATCGAAAACGTTTACTCATCAGCCTTGGCACTGTAAAACCAATGGTTG

ATGGTCTGGAGCTGATTTCATGGGTTATGGATTCTGCAAATGAAGTTGATG

CTGATATCATTTTGCAACTTGCAATAAATGCTCGTACTGGATTACGAAAAC

TACCATCAAATGTACGTCTGGTTGACTGGATACCTATGGGTGTATTCCTTA

ATGGAGCTGATGGATTTATTCATCATGGTGGCGCAGGTAATACCCTGACA

GCGTTGTATAGTGGGATACCACAGATTGTGTTTGGCGAAGGTGCAGATCG

CTCTGTTAATGCAGAAATTGTTGCGATGCGTGGGTGTGGGATTATTCCGGA

CAAGCATGGACTGACCAGTGATTTGGTAAATCGCCTGCTTTATGATGATTC

ACTACGCTTCTGTTCAGATCAGGTAGCCGCTGAAATGGCTGAACAACCCA

GTCCTGCAGAGATCGCAGAGGTTTTGATGAGAAAATTAAAAAACAACGG

GAAATAA.
```

-continued mchC gene sequence:

(SEQ ID NO: 2)

ATGAGTCATCAGTGTTCACTTTCTGAACTGAATGAAAACCTGGTGC

CTTTCACTGCCAGGCAGATCAAGTCCTCATTAATCTGGTGTGCAGAGGAT

GTCAGAAATCCAGGCGAGCTGCAAAATGCCTGCAGTTATATTATCGATCC

TGACAGTACGGCTTCTGCCAAAGTGTTCCATGCAGAGCGCTATGGTGGCA

GTGGTATTCAGCGTAATGGAGGTGGTGCACGTTGTGGGTTTGATGGTAAC

TACCAGGTTAAAGGAATAGGAAGTAATCCGTTGGTTGGTGAAGGTACTGA

CGAACGTCATTCTAATGGTGCACTCGGCGCTGTTCATGCAATATATGAGG

CTTTGTGGGGAGAAGTACTGGCTCAAATATTACCTTATAGTGCTGTGCGGG

TTCGGGCGGTTTTACTTACAGATCTCTATACTGAAAAGGCATTTGAGCGCT

CCGGTATGAAATCACGAAGAGCCCTGTTGGTACGTGAGCCTGTTGTTCGC

CCGGCGCATTTTGAACGGGCACCATACTTCCAAGTAAAACCGGAGTATTC

CAGTCAGTTAATTCACGATGCCTGTCGGGTTAGATCTGTGATCCACAAGCT

GCCAGGATATCTACCTGTACCACCGGAAGAAATTGATGCTGAAGCACGAA

CTGATCCCCGGATTTATTGCATTGAGGGATTATGTGAACTGGCACGTCGTG

AGGCCTGGCAAATGGCATTTTGTCGAACACGTTTCCTGAGATTGACAACTT

CTCCTTCTAATATTGCAATGGATGGCAGATTAATGGATTTTAACGGACTCA

GTTGCTCGTTTCCGGGAGATTCCCCAGCTGATTTTGGGTATAAACTAAGAT

TAGCTGAACTGGCAAAAGAACCGATGGTACTTATGCAAGGGCTGTCTGAT

CTCTGCTTGTATATCGGAAAATATATGTTTGACCCTGACTTCACTCTTGCA

GCCCGTTTGAAGGTTGAGGAGATATTTCAGAAAACTTTTCATGAAGCATG

TTATTACTGTTATCTAGAACTGTTGGGTATTCCTGGAGAATTTATAACACA

AAAAGAGATACCTGATATATTGAAACAACTGGTTAACAGTTTTGTTGCATT

ACTCAATAAATACTGCGAGAAATCACATGCCCAAGATATTGTCAATCAGG

ATGGTTCACCATTGCAAAAGTTGGTTGTGACGCTAATCCATCATAGGCAT

AATCAAAAGCAGGCACTGAATAGTAGCATCAAGAATGATGTTTATTTCAC

CGTTGCACAACAGTGTTTTTCCCAGACTATCCACTGGCTGACGCAAGGCA

GTACCAGACGTCAGATAAATGCTTCATTACTCCTGAAAGAAATTGAACAT

CATACCATGAAAAGGCTGCAACCCAGGGAAGAGCTGAGGAAAGAGAATA

TGTGCGAAAAAATTGCCATCCTGCTGGATAATCATGGCGATGATCCCCTTT

TTTTACAAGAAGCAATTTCTGATATGAAAAATTTTATGCTTAAGTTTTCCA

GAGATGCATTTGGATATCTTGAACCGATAAGAAACACAGTGTAA.

mchD gene sequence:

(SEQ ID NO: 3)

ATGTCTTATATAAGGGAAACCATCAGAGGAAAAGATGAATGGACT

GTTTATGAACAGATAGGTTTTGCGGTCAGTTGTATGCTCTACAATCGTAAT

TACAGTCTGTATCCGGTGTTAACCATTCAATACTGGACTGAATATGCGATA

CAGCATAATCAGATTAAATTCCTGTTTGATTCACGAGGTTTTCCACTGGCG

TATATAACCTGGGCATATCTTGAGGCTGATACGGAAGCGCGCCTGCTCAG

GGATCCAGAATTCAGGTTGCATCCGTCTGAATGGAATGAAGATGGAAGGA

TCTGGATCCTGGATTTCTGTTGTAAACCAGGCTTTGGTCGAAAAGTTATTG

ACTATCTCATACAGCTTCAGCCATGGGGGAAGGAGAAGTACGATGGTTA

```
AGCAGGCGAAAGAAAATTGTGACATACATCCCTGAGCGGCTGCATAAAA

CGTAG.
```

The mchB genes encodes the pre-Microcin H47 peptide. Once the peptide product of the mchB gene has gone through modification and secretion steps, the pre-Microcin H47 peptide becomes Microcin H47.

```
mchB gene sequence:
                                        (SEQ ID NO: 4)
ATGCGAGAAATAACAGAATCACAGTTAAGATATATTTCCGGGGCG

GGAGGTGCGCCAGCGACTTCAGCTAATGCCGCAGGTGCTGCAGCT

ATTGTTGGAGCTCTCGCCGGAATACCTGGTGGTCCACTTGGGGTT

GTAGTTGGAGCCGTATCTGCCGGTTTGACAACAGCAATTGGCTCG

ACCGTGGGAAGTGGTAGTGCCAGTTCTTCTGCTGGTGGCGGTAGC

TAA.
```

The mchE and mchF genes encode secretion proteins, which are necessary for MccH47secretion out of the cell.

```
mchE gene sequence:
                                        (SEQ ID NO: 5)
TTGTTTCGTCAGGATGCTTTAGAAAACAGAAAATGAAGTGGCAGGGACGGGCAATATTA

CTTCCCGGAATACCACTATGGTTAATCATGCTGGGA

AGCATTGTGTTTATTACGGCATTTCTGATGTTCATTATTGTTGGTACCTATA

GCCGCCGTGTTAATGTCAGTGGTGAGGTCACAACCTGGCCAAGAGCTGTC

AATATATATTCAGGTGTACAGGGATTTGTTGTCAGGCAATTTGTTCATGAA

GGGCAGTTGATAAAAAAGGGGATCCTGTTTATCTGATTGACATCAGTAA

AAGTACACGTAGTGGTATTGTCACTGATAATCATCGGCGGGATATAGAAA

ATCAGCTGGTTCGTGTGGACAACATTATTTCCCGTCTGGAAGAAAGTAAA

AAAATAACGTTAGATACCCTGGAAAAACAACGTCTGCAATACACAGATGC

GTTTCGTCGCTCATCAGATATTATACAGCGTGCAGAGGAAGGGATAAAAA

TAATGAAAAACAATATGGAGAATTACAGAAACTATCAGGCAAAAGGGCT

GATTAATAAAGATCAGTTAACTAACCAGGTGGCATTATATTATCAGCAAC

AAAACAATCTTCTCAGCCTGAGCGGACAGAACGAACAGAATGCCCTGCAG

ATAACCACTCTGGAGAGTCAGATTCAGACTCAGGCTGCAGATTTTGATAA

CCGTATCTACCAGATGGAACTGCAACGGTACGAGTTACAGAAAGAACTGG

TTAACACTGATGTGGAGGGCGAAATTATTATCCGGGCGTTGACTGACGGG

AAAGTTGACTCCCTGAGTGTCACTGTCGGGCAAATGGTCAATACCGGAGA

CAGCCTTCTGCAGGTTATTCCTGAGAACATTGAAAACTATTATCTTATTCT

CTGGGTCCCAAATGATGCTGTTCCTTATATTTCGGCTGGTGACAAAGTGAA

TATTCGTTATGAAGCCTTTCCGGCAGAAAAATTTGGGCAGTTCTCTGCTAC

GGTTAAAACTATATCCAGGACTCCTGCGTCAACACAGGAAATGTTGACCT

ATAAGGGTGCACCACAGAATACGCCGGGCGCCTCTGTTCCCTGGTATAAA

GTCATTGCGATGCCTGAAAAGCAGATTATCAGATATGACGAAAAATACCT

CCCTCTGGAAAATGGAATGAAAGCCGAAAGTACACTATTTCTGGAAAAAA

GGCGTATTTACCAGTGGATGCTTTCTCCTTTCTATGACATGAAACACAGTG

CAACAGGACCGCTCAATGACTAA.

mchF gene sequence:
                                        (SEQ ID NO: 6)
ATGACTAACGGGAGTTTCAGACAAATTATAAATCAGCTTGATATGC

GCTGGCGACGTCGTGTTCCGGTTATTCATCAGACGGAGACCGCTGAATGT
```

-continued

```
GGACTGGCCTGCCTGGCAATGATATGCGGTCATTTTGGTAAGAATATTGA
CCTGATATCTCTTCGCCGGAAGTTTAATCTCTCGGCCCGTGGAGCAAACCT
TGCAGGAATCAATGGAATAGCGGAGCAGCTGGGGATGGTCACCCGGGCT
CTTTCACTGGAGCTGGATGAACTTGGTGCCCTCAAAATGCCGTGTATTCTC
CACTGGGATTTCAGTCACTTTGTCGTGCTGGTCAGCGTAAAGCGTAACCGT
TATGTACTGCATGATCCGGCCAGAGGCAGAAGATATCTCGGTCGGGAGGA
AATGAGCCGGTATTTTACGGGCATTGCACTTGAGGTCTGGCCTGGAAGTG
AATTCCTGGCGGAAACCCAGCAGATCCGCATAAGTCTCCGTTCACTGATT
AACAGTATTTACGGTATTAAAAGAACACTGGCGAAAATTTTCTGTCTGTCA
GTTGTAATTGAAGCAATCAATCTGGTAATGCCGGTGGGGACTCAGCTGGT
TATGGATCATGCGATTCCGGCGGGGACAGAGGGCTGCTGACGCTTATTT
CTGCTGGCCTGATGTTCTTTATATTGCTCAGGGCCGCGGTGAGTATGCTGC
GTGCATGGTCCTCACTGGTTATGAGCACGCTCATCAATATACAGTGGCAG
TCGGGTCTGTTTAACCATCTTCTCAGACTGCCGCTGGCGTTTTTTGAACGC
CGTAAATTAGGTGATATCCAGTCGCGTTTTGGCTCCCTTGACACTTTGAGG
GCCACCTTTACCACCTGTGTGGTTGGGGCAATCATGGACAGTATTATGGTT
GTGGGGTTTTTGTGATGATGCTGTTATATGGAGGATATCTTACCTGGATA
GTGCTCGGTTTTACCATGGTTTACGTTCTTATTCGTCTGGTGACATACGGCT
ATTACCGGCAAATATCGGAAGAAACTCTTGTCAGGGGGGCCCGGGCCAGC
TCCTATTTTATGGAAAGCCTGTATGGTATTGCCACGGTAAAAATCCAAGGT
ATGGCTGGGATCCGGGGAACACACTGGCTTAACCTGAAAATAGATGCGAT
CAATTCAGGTATTAAGTTAACCAAGATGGATTTGCTCTTCGGGGGGATAA
ATACTTTTGTTGCCGCCTGTGATCAGGTGGCGATTTTATGGCTGGGTGCAA
GCCTTGTGATCGATAATCAGATGACAATAGGGATGTTTGTGGCATTTGGTT
CTTTTCGTGGGCAGTTTTCGGATCGGGTTGCTTCGCTGACCAGTTTTCTTCT
TCAACTGAGAATAATGAGTCTGCATAATGAGCGCATTGCAGATATTGCAC
TACATGAAAAGGAAGAAAAGAAACCGGAAATTGAAATCGTTGCTGACAT
GAGCCCGGTTTCACTGGAAACCACTGATTTAAGCTACCGGTATGACAGCC
AGTCAGCACAGGTATTCAGTGGTCTGAATTTGTCTGTGGCTCCGGGAGAA
AGTGTGGCTATAACTGGTGCCTCCGGTGCCGGAAAAACCACATTAATGAA
AGTATTATGTGGACTGTTTGAACCAGATAGTGGAAAAGTACTGGTTAATG
GCACGGATATACGTCAACTTGGAATAAATAATTATCACCGTATGATAGCC
TGTGTTATGCAGGACGACCGGCTATTTTCAGGATCAATTCGTGAAAATATC
TGTGGGTTTGCAGAAGAAACAGACGACGAATGGATGACAGAATGTGCCA
GAGCAAGTCATATTCATGATGTGATAATGAAAATGCCAATGGGGTATGAA
ACGTTAATAGGTGAACTGGGGGAAGGTCTTTCCGGCGGTCAAAAACAGCG
TATATTCATTGCCCGAGCTTTATACCGGAAACCTGGAATATTATTTATGGA
TGAGGCTACAAGTTCTCTTGATACAGAAAGTGAACGTTTCGTGAATGCTG
CCATAAAAAAAATGAATATCACCCGGGTGATTATTGCACACAGAGAAACT
ACGTTGAGAACTGTTGACAGGATTATTTCTATTTAA.
```

The mchI gene encodes an immunity protein.

mchI gene sequence:
(SEQ ID NO: 7)
ATGAGTTATAAAAAACTGTACCAATTGACGGCTATATTTAGTTTAC

CTCTTACTATCTTATTGGTTTCACTTTCATCCCTTCGGATTGTTGG

CGAAGGGAATTCTTATGTTGACGTTTTTCTAAGCTTTATAATATTT

CTTGGTTTTATTGAGCTGATTCATGGGATTCGAAAGATTTTGGTCT

GGTCAGGCTGGAAAAACGGAAGTTAA.

mchX gene sequence:
(SEQ ID NO: 8)
ATGGAATTTGCTACAAACAGGGTTACTGTAAATGACAGTCGGTCAG

CACTGTCATCAACTTTGCTGTTGTCTTTGATCATGAGCGCCACTCT

ACTGGAATATTCTTTATCGATGACCTGA.

mchS1 gene sequence:
(SEQ ID NO: 9)
ATGAAAAACTATCTTTTCCAGACTCCCGAAGATATTTGTGTACAGT

TAAAAAAAATGACACATCCTGTCACAATAAGAACAACAGATATTGC

TAATTTCTGGCACTATCTTGAGTCAGCAACTCTTCCGGTGATCACA

AAAAGCACCACTACAGAAAATCGGGAGGTTACATTTCTGTGGCGCT

CAGAGAAAGCAGTGCAAGGCGTATATCTTCGCCTGAATCGTGTTAC

AGATAAAAAAGATGTCAAAAAAGGACTAATGACTCATATCCCTTCG

ACAGATATCTGGATGCTGACACTGGTGTTACCAGCTTCATATCGGG

GCTCATACTCATTTATAGAAATTCCCACAGATATGACACAAAAAGA

CATATTTCAACTAGGAAGTCGCTTCTCTCCATTACCCGGTAAATCT

GATCCATTTAACAAAACAGCAGAAATAAATATACGAGGATTCGGAG

AATCAGTCCTTTCTCTTGATATGGCTCCTGAACAAAAGGAATGGGA

TGATACTTCCCATAAATGTACAGGTATTCTTTCAACATTACATTCC

TTTGTTGCAGGATATCAACGCCGGATTCGTTTATATTTTCCCCAGA

ATCCAACATCAGTACCTCTTGGATTACTTGTGTTACCTGATGCTGA

AATATGGTTTGACCGGATGGATATTACCCGGGCATTAGATATGGCC

ATTACCACTGGTCATATTGCGCCAATGGCAATTATGGGGATAGACA

ATATTAATGAATCTGATCGTATGAATATACTGGGAGGCAATAAAGA

ACTTATCTTTGATATAGCGGAAAATCTGATACCCCAGTTATACAGA

GACTACCCGAATATCGTATGGGCTGGTCGTTCTAATACTATACTGG

CCGGTCAGAGCCTCGGTGGAGTGACAGCACTGATGGCAGCTATATA

TGCGTCGACAACATTTGGTACAATCATTAGCCACTCACCTTCAATG

TGGTGGAACCCTGACCAGGGCAGCCCGATTTTGTTTACTGAGAATG

ATATCTCCTGGGTAAGTGAGCAGATACTTTCAGCGCCTCCGAAAGA

TGTAAATATCCAACTTGGAGTCGGTTCTTTAGAAGGTACAACCGTC

TCACATGTTCAGCGGTTGCATCAGTCGTTAATCGCAGCAGGTTTGG

AAAGTAACCTCACTGTCTATGCCGGTGGTCATGATTATGCCTGGTG

GCGCGGAGCAATTATTGATGCATTAGCAAATTATAATTGCAGGAAG

ATATCAGATAATAACTTTGTGTAA.

mchS4 gene sequence:
(SEQ ID NO: 10)
ATGAATTGTGATAATAATCACAGAAATGAAGAATTCATTGTTACCT

TTGATAAAGGCAACAAGCAAGACAATTCAAGACGAAAACACGATAA

TTTTCCTATAGAGGTAGAATCCTCCGTAGAGCTGGAGACACACTGT

ATCACAAATAATAAGTCGGCTTCCGGTATAGTAACACATGACTATG

ATGCCGATTATATTTGTGGTTGTGGTGAAATTATGTGTCCTGGTTG

CGGTCATGACCTATAA.

In some embodiments, the microcin that can be used in the compositions and methods as described herein is microcin J25. A detailed description regarding microcin J25 is described, e.g., in Bayro, Marvin J. et al. (2003). Structure of antibacterial peptide microcin J25: a 21-residue lariat protoknot. Journal of the American Chemical Society 125.41: 12382-1238, which is incorporated by reference herein in its entirety.

ttr Operon and Tetrathionate Sensor System

During gut inflammation, reactive oxygen species produced by the host react with luminal thiosulfate, resulting in production of tetrathionate (Winter et al. (2010) Gut inflammation provides a respiratory electron acceptor for *Salmonella*. Nature 467, 426-429.). *Salmonella* species utilize the gene products of the ttr operon, which provide this pathogen with the ability to utilize tetrathionate as a terminal electron acceptor, conferring a growth advantage over the competing microbiota during inflammation conditions (Winter et al. (2010) Gut inflammation provides a respiratory electron acceptor for Salmonella. Nature 467, 426-429.). As used herein, the term "ttr operon" refers to an operon comprising at least one gene selected from the group consisting of ttrA, ttrB, ttrC, ttrR, and ttrS.

The ttrBCA genes (ttrA, ttrB, ttrC) of *Salmonella*, encoding the three subunits of tetrathionate reducatase, which has tetrathionate reductase activity. The ttrBCA promoter (Pttr) is positively regulated by TtrR in the presence of tetrathionate, and by Fnr, under anoxic conditions (Winter et al. (2010) Gut inflammation provides a respiratory electron acceptor for *Salmonella*. Nature 467, 426-429.). TtrS, a membrane-bound sensor histidine kinase (SK) that phosphorylates the cytoplasmic response regulator TtrR in the presence of tetrathionate. Phosphorylated TtrR (TtrR~P) activates transcription of the tetrathionate reductase operon, ttrBCA, via the ttrB promoter (Pttr). However, Pttr is repressed by $O_2$ and nitrate via the global regulator FNR. Furthermore, FNR is required for transcription from Pttr.

Together the ttrB promoter (Pttr), ttrS, and ttrR constitute a tetrathionate sensor system.

ttrA gene sequence:
(SEQ ID NO: 11)
ATGGCTAATTTAACCCGTCGTCAGTGGCTAAAAGTCGGTCTCGCCGTCGGTGGGATGGT

CACTTTTGGTCTGAGCTACCGTGATGTGGCGAAACGC

GCAATTGATGGCCTGTTAAACGGGACGTCCGGCAAGGTAACGCGCGACCG

```
CATCTTTGGCAATGCGTTAATTCCGGAGGCGCAGGCGCAAACACACTGGC

AGCAAAATCCACAACAAACCATCGCCATGACGCAATGCTTCGGCTGTTGG

ACACAGTGCGGTATCCGCGCCCGGGTTAATGCCGATGGCAAAGTGATACG

CATCGCCGGCAATCCCTATCACCCCTTGTCGCAGGAACACCCGATTGACTC

GTCCGTCCCTTTTAGCGAAGCCATGGAGCAACTGGCGGGAGAAAGCGGTC

TTGACGCCCGCTCAACCGCCTGCGCGCGCGGCGCCACGCTGCTGGAAAGC

CTGTACAGTCCGCTACGACTGCTTGAACCGATGAAACGCGTGGGTAAACG

CGGCGAAGGGAAATGGCAGCGCATCAGCTTTGAGCAACTTATTGAAGAA

GTCGTGGAAGGCGGCGATCTGTTTGGCGAAGGTCATGTGGACGGACTGCG

CGCTATTCATGCGCCGGATACGCCAATTGACGCAAAGCACCCCAGTTTCG

GGCCCAAAACCAATCAGTTACTGGTCACGAATACCAGCGACGAAGGCCGC

GATGCGTTTCTGCGTCGTTTTGCGCTAAATAGCTTCGGCAGCAAGAATTTC

GGCGCGCATGGCGCCTACTGTGGACTGGCTTACCGGGCCGGCTCCGGGGC

ATTGATGGGCGATCTGGATAAAAACCCGCATGTCAAACCCGACTGGGAAA

ACGTGGAGTTTGCGCTCTTTATGGGCACCTCCCCGGCACAGTCCGGCAATC

CGTTTAAACGCCAGGCACGTCAGTTGGCGAGCGCCCGACTGCGTGAGAAT

TTTCAATACGTCGTGGTCGCCCCCGCCCTCCCCTTATCAACGGTGCTCGCC

GATCCTCGCGGTCGCTGGCAACCGGTCATGCCCGGCAGTGATTCGGCGCT

GGCAATGGGGATGATCCGCTGGATCATGGATAATCAACGTTATAATGCTG

ATTATCTGGCGATTCCCGGCGTACAGGCGATGCAGCAGGCCGGCGAGCAA

AGTTGGACCAACGCCACGCACCTGGTCATTGCGGATGAGCTGCCGACGCT

TGCCGGACAACACCTGACGCTGCGCCATCTTACGCCCGATGGCGAAGAGA

CCCCTGTCGTACTGAATACCGACGGCGAGTTGGTCGATGCGTCCACTTGCC

GACAGGCACGGCTTTTCGTGACGCAGTACGTTACGCTCGCCGACGGCCAA

CGGGTCACGGTGAAGAGCGGGTTGCAACGCCTGAAAGAGGCGGCAGAAA

AGCTCTCGTTGGCGCAATACAGCGAACAGTGCGGCGTGCCGGAAGCGCAA

ATTATCGCGCTGGCGGAAACCTTTACCAGTCACGGACGTAAAGCTGCGGT

CATCAGTCACGGCGGCATGATGGCCGGCAATGGGTTTTATAACGCCTGGT

CGGTCATGATGCTTAACGCGCTGATCGGCAACCTCAGCTTGTCCGGCGGC

GTCTTTGTCGGCGGCGGCAAATTCAACGGCGTTAGCGACGGCCCCCGCTA

CAACATGAACAGTTTTGCCGGAAAAGTGAAACCGTCCGGGTTAAGTATTG

CCCGTAGCAAAACCGCTTATGAAGCATCGGAAGAATACCGCGACAAAATT

GCCGGTGGGCAATCCCCTTATCCAGCCAAAGCGCCGTGGTATCCCTTTGTG

GCAGGCCAGCTTACCGAACTGTTGACCTCCGCGCTCGAAGGCTATCCTTAT

CCGCTTAAAGCCTGGATTTCCAATATGAGCAACCCGTTTTACGGTGTTCCC

GGTCTACGCGCCGTGGCGGAAGAAAAACTAAAAGACCCTCGCCGACTGCC

GCTCTTTATCGCGATTGACGCCTTTATGAATGAAACGACGGCGCTGGCGG

ATTACATTGTGCCGGATACGCACAATTTTGAGAGCTGGGGCTTTACGGCG

CCCTGGGGCGGCGTAGCCAGTAAAGCCACTACCGCCCGCTGGCCGGTTGT

CGCCCCCGCCACTCACCGCACGGCGGACGGGCAACCTGTCTCAATGGAAG
```

```
CATTTTGTATTGCGGTAGCAAAACGGCTCCATCTGCCCGGCTTCGGCGACC

GGGCGATAACCGATCCGCAGGGCAATACTTTTCCACTGAACCGGGCGGAA

GACTTCTATCTGCGCGTAGCCGCTAATATCGCCTTTATGGGCAAGACGCCG

GTCGCGCTGGCAAATCAGGAAGATATTTCGCTTACCGGCGTCAGCCGCAT

TCTGCCAGCAATTCAGCACACGCTTAAAGCTGATGAGGTCGGTCGCGTGG

CGTTTATCTACTCGCGTGGCGGCCGGTTTGCGCCCGAGGATAGCGGCTAT

ACGGAGCAACGGTTAGGTAACGCGTGGAAAAAACCCTTACAGATCTGGA

ATGCAGATGTCGCCGCCCACCGTCACGCCATCACCGGGGAGCGCTTCAGC

GGTTGCCCGGTCTGGTATCCGGCGCGTTTGTCAGATGGTCGTGCGATTGAC

GACCAGTTTCCCATTGGGCAATGGCCGCTGAAACTGATTTCATTTAAATCA

AATACCATGTCCAGCTCAACAGCCGTCATCCCGCGCTTACACCATGTGAA

GCCAGCAAACCTGGTGGCGCTGAATCCGCAAGACGGCGAGCGTTATGGAC

TGCAACATGGCGATCGGGTACGGATCATTACGCCGGGCGGTCAGGTCGTG

GCGCAAATCAGTTTGTTAAATGGCGTGATGCCAGGCGTCATCGCCATCGA

ACACGGATATGGCCACCGCGAGATGGGCGCAACGCAGCACTCTCTGGATG

GCGTGCCTATGCCGTATGATCCACAAATCAGGGCAGGCATAAATCTTAAC

GATCTGGGCTTTGCCGATCCGACAAGAACCATTACCAACACCTGGCTCGA

CTGGGTTTCTGGCGCGGCAGTACGTCAGGGGCTGCCGGCAAAAATCGAGC

GTATATAA.

ttrB gene sequence:
                                                   (SEQ ID NO: 12)
ATGTGGACGGGAGTCAATATGGACAGCAGTAAACGGCAATTTCTC

CAGCAGCTTGGCGTCCTGACCGCTGGCGCCTCGCTGGTTCCGCTGGCTGA

AGCGAAATTTCCTTTTTCGCCGGAGCGGCATGAAGGCTCTCCCCGACACC

GTTACGCCATGCTTATCGATCTGCGGCGTTGTATCGGCTGTCAGTCCTGTA

CCGTAAGTTGCACTATTGAAAACCAAACGCCGCAAGGCGCGTTTCGTACG

ACGGTGAACCAATACCAGGTCCAGCGTGAAGGTAGTCAGGAAGTCACGA

ATGTGCTGTTGCCGCGTCTGTGCAACCATTGCGATAACCCCCCCTGTGTGC

CGGTCTGCCCGGTACAAGCCACCTTTCAGCGGGAAGATGGCATTGTGGTG

GTGGATAACAAACGCTGCGTCGGCTGCGCCTATTGTGTCCAGGCGTGTCC

TTACGACGCCCGATTTATCAATCATGAAACGCAAACTGCCGATAAATGCA

CGTTTTGCGTCCATCGTCTGGAAGCCGGACTGTTACCCGCTTGCGTAGAGT

CCTGCGTCGGCGGCGCGCGTATTATTGGCGATATCAAAGATCCCCATAGC

CGCATCGCCACCATGCTTCATCAGCATCGCGACGCTATCAAGGTATTAAA

GCCGGAAAACGGCACGTCGCCCCATGTTTTCTACCTGGGTCTGGACGACG

CCTTTGTCACCCCATTAATGGGCCGTGCGCAGCCCGCGCTTTGGCAGGAG

GTCTGA.

ttrC gene sequence:
                                                   (SEQ ID NO: 13)
ATGACGCATTCACTCATCATTGAAGAAGTGCTGGCTCACCCGCAGG

ACATTAGCTGGCTGCCGTGGGCGGTACAATATTTCTTTTTTATTGGCATTGCC

GCCTGCGCCGCACTGTTTGCCTGTTATCTTCACTGGCGGAAAAAAGACGCC

GCAACAGAAGAAAATCGGGCATTACTGATTGCCATTACCTGTGCGATTACC
```

```
GCACCGCTGGCGCTGACGGCGGATCTGCACCAGACCGCCCGCGTCTGGCA

TTTCTATGCCTGGCCGACGCCCTGGTCGTGGATGCCCTGGGGAGCGTTATTC

CTGCCGCTGTTTACCGGATTTCTCGCTCTGTGGTTCCTGGCGCAGCAGATTA

AACGATTATTCAATAAAAGTTACAACGTCACTAAATGGTTGGCGTTAGCCA

GCGCGCTTTGCGCGGTGGGCCTGTTGATTTATACCGGCCGCGAAGTCTCCG

TTGTGCTGGCGCGCCCAATCTGGTTTAGCTACGCCTTCCCCGTGGCGATGTT

TCTTAGCGCCTTACAGGCATTCTTCGCGCTGATGATTGTCGCCGCCCGACAC

GACTCGGTAAGGCTGCCAAAAATATTGTGGGGACAAATCTGGACGCTGGC

GGCGCTGGGGCTGGTTGTGGCCATGTGGGTTAGCGGCGATACGCTTTCCGG

CACGGCAATCCGTCAGTGGATTACCGTCGCCCTGTCAGCCAAATATTACGCT

GTCGGCTGGGTAGCGCTGTGGGTATGCACACTGCTGTTCTGTAGCCTGGCG

CTACGCCATCCGTTATCACAGCTAAGACGCGTCCTGCTGGTTCTCAGCGCG

CTGGCGCTATGTTGGCTGATGCGCTGGACATTGTTGATTCAGGTACAAACC

GTCCCCAAGTTCAACGCGCAATTTAACCCTTACTCGTTACCAGGCGGAACG

GATGGCTGGCTGGCTATTCTCGGCACCTTCGGCCTGTGGATAGCGCTACTG

ATTATTATTCGTGAAACGCTGAACGGACTCACCAGGAGATTACAACATGGC

TAA ttrS gene sequence:
                                              (SEQ ID NO: 14)
GTGAGAGGTAAAACCGTAAGGCGCCTGGCGGTGTTGGCGGCAGTA

GGGCTACTTTGTCATGGCGCGTGGGCAGGGACGTGGAATATCGGTATTTT

GGCCATGCGCGGCGAGGCGTCTACGCGTAGCCACTGGCAACCGTTGGCAA

AGACATTAAGCCAACAGCTTCCAGGCGAAACCTTTCACATCCAGCCGCTG

GATCTGCATCAAATGCAGGAGGCCGTTAACCAGGGAACCGTGCAGTTTGT

GATAACCAACCCGGCGCAATTTGTCCAACTGAACAGCCATGCGCCGCTGC

GCTGGTTAGCTTCCCTGCGCTCCACGCGCGATGGGAAAGCGGTGAGTAAT

GTTATTGGCAGCGTGATTTTGACCCGGCGCGATAGCGGCATCACCACGGC

GCATGATCTCATCGGTAAGACCGTCGGCGCGATTGATGCTCAGGCGTTTG

GCGGCTATTTATTAGGCTATAAAGCGCTCAGCGACGCGGGCTTACGCCCG

GAGCGCGATTTTCATCTCCGTTTTACCGGATTTCCTGGCGATGCCTTAGTC

TATATGCTGCGCGAAAAAGCGGTGCAGGCGGCAATTGTGCCAGTGTGCCT

GTTAGAAAATATGGATCAGGAAGGATTGATTAATAAAAAGGACTTTATCG

CGCTGCTTTCCCGACCGACGCCCCTGCCTTGCTTAACCAGTACGCCGTTAT

ATCCTGACTGGTCGTTCGCGGCGCTACCTGCGGTAAGCGATGCGCTGGCG

GATCGCGTAACGCGAGCGCTATTCAACGCGCCCGCCGCCGCGTCATTTCA

CTGGGGCGCGCCTGCGTCCACCAGTCAGGTGGAAGCCTTGCTGCGTGATG

TTCGTCAGCACCCTCAGCAGCGTCGACTGTGGCTGGATGTCAAAAGTTGG

TTAATCCAGCACCAGCTAATGGTCGGCGGCGTGATTCTGGCGTTCTTGTTG

CTCACGCTCAATTATATTTGGGTCATGCTGCTGGTGCGTCGACGTGGAAAG

CAACTGGAACGTAATAGCGTAGTTCTTCATCAGCATGAGCGGGCGCTGGA

AACCGCCCGGCAAATGAGCGTGTTGGGTGAAATGACCTCCGGGTTTGCCC
```

```
-continued
ATGAGCTTAATCAGCCGCTTTCCGCGATTCGACATTATGCCCAGGGGTGCC

TGATTCGACTGCGCGCTGCAGATGAACAGCATCCCTTGCTGCCGGCGCTG

GAGCAGATTGACCAGCAGGCGCAACGCGGTGCGGATACTCTGCGTAACCT

GCGTCACTGGGTCAGCCAGGCGCAGGGCAACCCGGTGCTAACCGAAGCGT

GGAAGGCCATAGCCATTCGCGAGGCGATTGATCATGTCTGGCAATTGTTG

CGTATGGCGCAACAGTTTCCGACAGTGACTCTGCATACCGAGGTTAGCGC

TGCGCTGCGCGTAACGCTGCCGTCAGTGCTGCTGGAACAGGTGCTGGCGA

ATATCATTCTTAATGCGGCTCAGGCGGGCGCCACCCATTTATGGATCGTTG

CTGAACGCACTGAAAACGGCATCAGTATTGTTTTACAGGATAACGCCGGG

GGAATCGATGAGGCGCTATTACGTCAGGCGTTTCAGCCGTTTATGACCAC

CCGTAAAGAGGGGATGGGCTTAGGGCTGGCGATTTGCCAGCGGCTGGTGC

GGTATGGGCGGGGCGATATCAGCATCAGGAACCAGACCGCGCCGGACGG

TCTGTCGGGAACGGTGGTTACGATACATTTCTTACATGAAAATGGGGGCA

GGGATGGCGACAATTCATCTACTGGATGA.

ttrR gene sequence:
                                                 (SEQ ID NO: 15)
ATGAAAATGGGGGCAGGGATGGCGACAATTCATCTACTGGATGAT

GATACGGCGGTCACTAACGCGTGCGCGTTTTTACTGGAAAGTCTGGGATA

TGACGTAAAATGCTGGACGCAGGGGGCGGATTTTTTGGCGCAGGCCAGTC

TGTATCAGGCCGGGGTCGTATTACTGGATATGCGAATGCCGGTACTGGAT

GGGCAGGGCGTTCATGATGCGTTGCGCCAGTGCGGAAGTACCCTGGCGGT

TGTTTTTCTTACCGGGCATGGCGATGTACCGATGGCCGTGGAGCAGATGA

AACGCGGCGCCGTCGATTTTCTGCAAAAACCGGTATCGGTAAAACCGCTA

CAGGCGGCGCTGGAGCGTGCGCTGACGGTTTCATCGGCAGCGGTGGCGCG

TCGTGAGATTATACTGTGTTACCAGCAGTTGACGCCGAAAGAGCGTGAGC

TGGCCAGCCTGGTGGCAAAAGGATTTATGAACCGTGAAATTGCGGAAGCG

ATGAATATCGCGGTGCGTACCGTAGAGGTGCACCGCGCCAGAGTCATGGA

AAAAATGCAGGCCGGTAGCCTGGCGGAACTGATTAGGCGTTTCGAAAAA

ATGGCCTCGCCAGAGACCAGAATACGAACAACGTATGAGCCATGA
```

Vectors

This disclosure provides various vectors comprising microcin genes and controllable promoters (e.g., inducible promoters). In some embodiments, the vector is a plasmid (e.g., pBR322, pLJV3, pJPMcH47, pttrMcH47, and pEX2000).

The vector can include genes for various microcins, e.g., Class I microcins, Class IIa microcins, Class IIb microcins, and/or Class IIc microcins. In some embodiments, the vector can include a set of genes for a Class IIa microcin (e.g., MccH47, MccE492, MccM, MccG492, and MccI47). In some embodiments, the vector can include a set of genes for McCH47 and/or microcin J25.

In some embodiments, the vector includes a set of genes for MccH47. These genes are required to express a functional MccH47 that can inhibit the growth of other bacteria. In some embodiments, the set of genes includes one, two, three, four, five, six, seven, or eight genes that are selected from the group consisting of mchA, mchB, mchC, mchD, mchE, mchF, mchX, mchI, mchS1, and mchS4. In some embodiments, the set of genes includes mchA, mchB, mchC, and mchD. In some embodiments, the set of genes includes mchA, mchB, mchC, mchD, mchE, and mchF. In some embodiments, the set of genes includes mchA, mchB, mchC, mchD, mchE, mchF, mchX, mchI, mchS1, and mchS4.

In some embodiments, these genes can be located within one operon. Thus, in some embodiments, the operon includes one, two, three, four, five, six, seven, eight, or nine, or ten genes that are selected from the group consisting of mchA, mchB, mchC, mchD, mchE, mchF, mchX, mchI, mchS1, and mchS4. In some embodiments, the operon contains mchB, mchC, mchD, mchE, mchF, mchX, and mchI. In some embodiments, the operon contains mchA, mchS1, and mchS4.

In some embodiments, the set of genes or the operon is under the control of a controllable promoter. As used herein, the term "controllable promoter" refers to a promoter of which the initiation of transcription is controllable. For example, the initiation of transcription of a controllable promoter can be induced by a ligand, such as tetracycline, arabinose, galactose, isopropyl β-D-1-thiogalactopyranoside (IPTG), allolactose, etc. In some embodiments, the controllable promoter is rhaPBAD or Pttr.

A high level of microcins may be harmful to a subject, thus, according to the present disclosure, mechanisms can be introduced to the genetically engineered microorganisms to control the transcription of the genes or the operon, and thus control the level of microcins. The transcription of the microcin genes can be controlled by a controllable promoter. Some exemplary controllable promoters include, but are not limited to, Pttr promoter or pBAD promoter. The pBAD promoter is found in bacteria and was originally part of the arabinose operon that regulates transcription of araB, araA, and araD. Transcription initiation at the pBAD promoter occurs in the presence of high arabinose and low glucose concentrations. Upon arabinose binding to AraC, the N-terminal arm of AraC is released from its DNA binding domain via a "light switch" mechanism. This allows AraC to dimerize and bind the I1 and I2 operators. The AraC-arabinose dimer at this site contributes to activation of the pBAD promoter. Additionally, cyclic AMP receptor protein (CAP) binds to two CAP binding sites upstream of the I1 and I2 operators and helps activate the pBAD promoter. In the presence of both high arabinose and high glucose concentrations however, low cAMP levels prevent CAP from activating the pBAD promoter. In the absence of arabinose, AraC dimerizes while bound to the O$_2$ and I1 operator sites, looping the DNA. The looping prevents binding of CAP and RNA polymerase. Thus, without arabinose, the pBAD promoters are repressed by AraC. A detailed description of pBAD promoter can be found, e.g., in Schleif R. AraC protein, regulation of the L-arabinose operon in *Escherichia coli*, and the light switch mechanism of AraC action. FEMS Microbiol. Rev., (2010) 1-18, which is incorporated by reference in its entirety.

pBAD promoter sequence:
(SEQ ID NO: 16)
CCACAATTCAGCAAATTGTGAACATCATCACGTTCATCTTTCCCTGG

TTGCCAATGGCCCATTTTCCTGTCAGTAACGAGAAGGTCGCGTATTC

AGGCGCTTTTTAGACTGGTCGTAATGAA.

In some embodiments, the controllable promoter is Pttr and is activated in the presence of tetrathionate as the inducing agent. The vector can also include genes that are required to determine the level of tetrathionate. Thus, the vector can include one, two, three, four or five genes that are selected from the group consisting of ttrA, ttrB, ttrC, ttrS, and ttrR. In some embodiments, the vector includes ttrS and ttrR.

In some embodiments, ttrA, ttrC, and ttrB are located within one operon. In some embodiments, this operon further includes mchB, mchC, mchD, mchE, mchF, mchX and mchI. In some embodiments, this operon is under the control of Pttr.

Figures 6A, 6B, 6C:
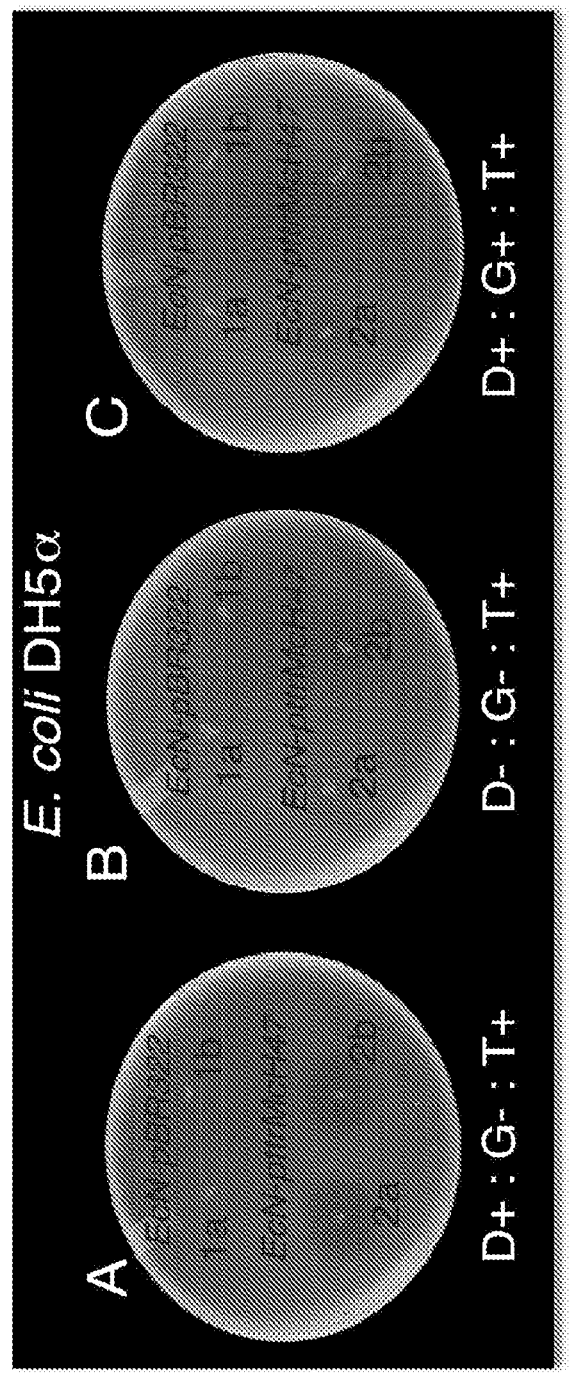
FIG. 6A is a representation of a plate with E. coli DH5α grown as a lawn and then challenged by addition of either EcN-pBR322 or EcN-pttrMcH47 to specific positions of the plate; plate was supplemented with 0.2 mM 2,2'-dipyridyl and 1 mM of potassium tetrathionate.
FIG. 6B is a representation of a plate with E. coli DH5α grown as a lawn and then challenged by addition of either EcN-pBR322 or EcN-pttrMcH47 to specific positions of the plate; plate was supplemented with 0.1% D-Glucose and 1 mM of potassium tetrathionate.
FIG. 6C is a representation of a plate with E. coli DH5α grown as a lawn and then challenged by addition of either EcN-pBR322 or EcN-pttrMcH47 to specific positions of the plate; plate was supplemented with 0.2 mM 2,2'-dipyridyl, 0.1% D-Glucose, and 1 mM of potassium tetrathionate.
Figure 7:
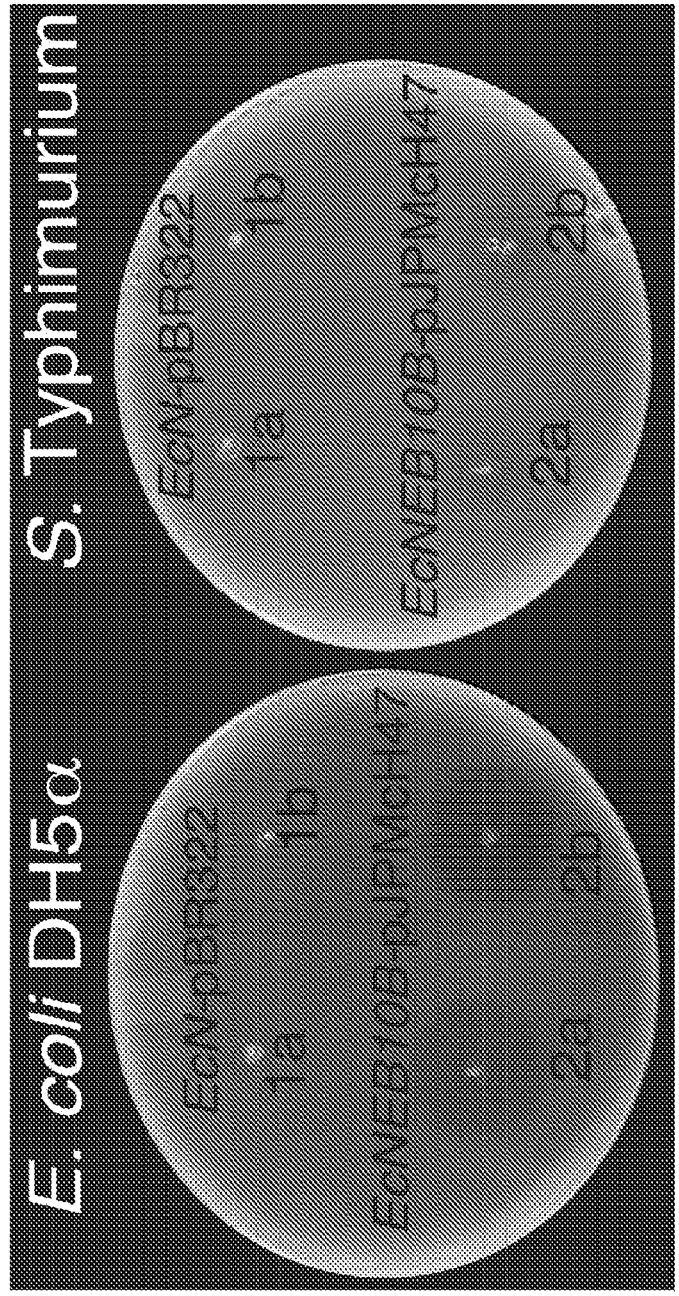
FIG. 7 are representations of plates with either E. coli DH5α (left) or S. Typhimurium (right) grown as lawns and then challenged by addition of either EcN-pBR322 or EcNEB10β transformed with pJPMcH47 (herein referred to as "EcNEB10β-pJPMcH47") to specific positions of the plates.
Figure 8:
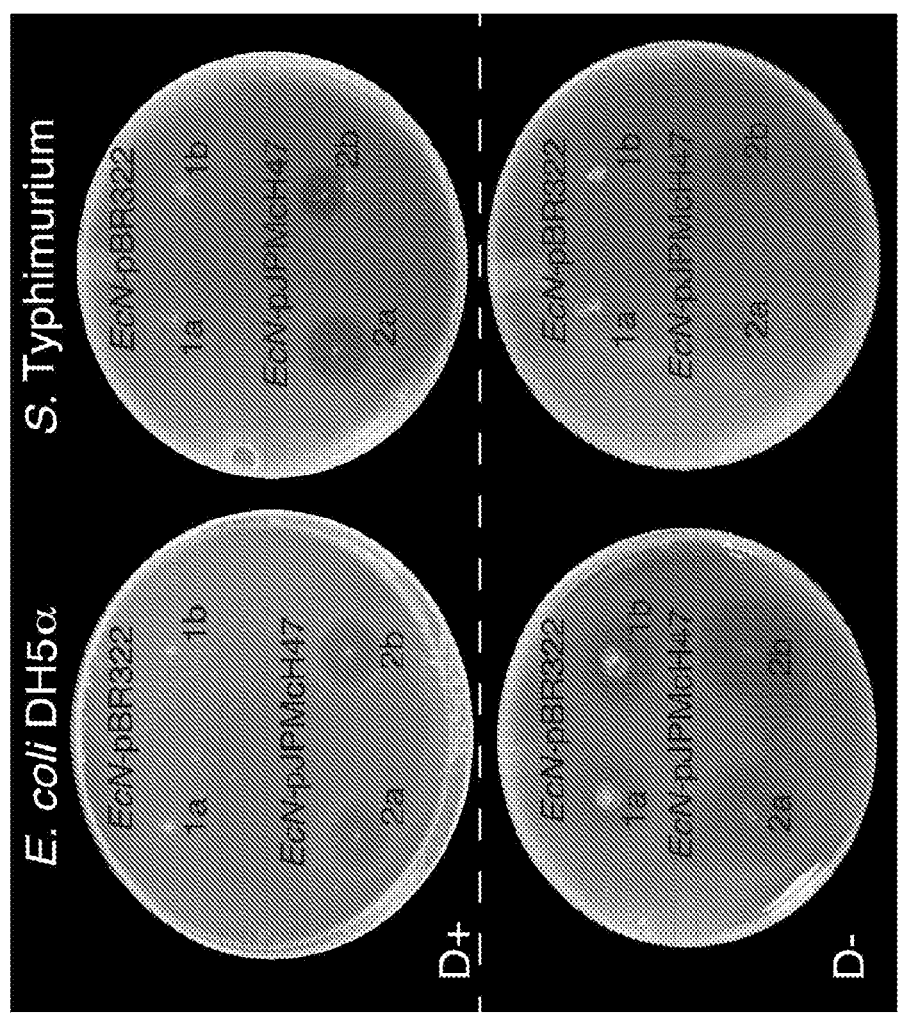
FIG. 8 are representations of plates with either E. coli DH5α (left) or S. Typhimurium (right) grown as lawns and then challenged by addition of either EcN-pBR322 or EcN-pJPMcH47 to specific positions of the plates; plates in top row were supplemented with 0.2 mM 2,2'-dipyridyl.

In some embodiments, the tetrathionate promoter (Pttr) is located immediately upstream of the mchXIB genes (mchX, mchI, mchB), and encoding them on a single transcript based on activation of the ttr promoter. The mchA can controlled by a constitutive promoter (e.g., J23119) (See e.g., FIG. 1B and FIG. 6A).

Pttr promoter sequence:
(SEQ ID NO: 17)
CCCAATATCCCTGTCAATTATGTTGTTTTAGATCAACAACAAGCCGG

GTATGTGGTTAACCACAATAGAGCGCACCCCGCCTCGATTTTTACAC

TGTAAATCATCGACATTTTTTATTCATTACACATGAACCAACATCGT

GACAAATGTTTCATTGTTGGCA.

J23110 promoter sequence:
(SEQ ID NO: 18)
TTGACAGCTAGCTCAGTCCTAGGTATAATGCTAG.

This disclosure further provides genetically engineered microorganisms comprising the vectors as described herein. In some embodiments, the vector are integrated into the genome of the microorganism, e.g., by recombinant DNA techniques. Thus, in one aspect, this disclosure provides an engineered strain of EcN harboring a plasmid-based system carrying mchAXIBCDEF and ttrRSBCA, capable of producing McCH47 in response to environmental tetrathionate, resulting in the ability to inhibit and out-compete *Salmonella*.

Genetically Engineered Microorganisms

Many microorganisms can be genetically engineered to treat bacterial infection as described herein. In some embodiments, a bacterium is used. In some embodiments, the bacterium is *E. coli* (e.g., *E. coli* Nissle 1917 or *E. coli* NGF-19). One useful *E. coli* strain is Nissle 1917 (EcN). *E. coli* Nissle 1917 is a Gram-negative species, which is easily cultured, easily genetically manipulated, able to colonize a human host, and easy to use for human probiotic applications. EcN is the active component of Mutaflor® (Ardeypharm GmbH, Herdecke, Germany), a microbial probiotic drug that is marketed and used in several countries. Clinical trials have shown EcN to be effective for maintaining remission of ulcerative colitis (UC), for stimulation of the of the immune system in premature infants, for treatment of infectious GI diseases, for the relief of constipation, and also for treatment of Irritable Bowel Syndrome in some patients.

In some embodiments, useful microorganisms that can be used in the methods disclosed herein include bacteria for making yogurt, e.g., *Lactobacillus delbrueckii* subsp. *Bulgaricus* and *Streptococcus thermophiles*.

A vector or a set of genes as described herein can be introduced into a microorganism, e.g., a bacterium, such as, *E. coli*, to generate a genetically engineered microorganism by known molecular biology, microbiology, and recombinant DNA techniques. These techniques are familiar to one of skilled in the art and are explained fully in the literature. See, e.g., Molecular Cloning: A Laboratory Manual (Michael R. Green, Joseph Sambrook, Fourth Edition, 2012); Oligonucleotide Synthesis: Methods and Applications (Methods in Molecular Biology) (Piet Herdewijn, 2004); Nucleic Acid Hybridization (M. L. M. Andersen, 1999); Short Protocols in Molecular Biology (Ausubel et al., 1990), each of which is incorporated herein by reference in its entirety.

In some embodiments, the vector or the set of genes is integrated into the bacterial or other microbial genome.

Methods of Treating Bacterial Infection

McCH47 has been shown to be active to inhibit various bacteria, e.g., gram-negative bacteria. As used herein, the term "gram-negative bacterium" refers to a bacterium that do not retain the crystal violet stain used in the Gram staining method of bacterial differentiation. Gram-negative bacteria include, e.g., proteobacteria, cocci, bacilli, etc. The proteobacteria are a major group of gram-negative bacteria, including *Escherichia coli* (*E. coli*), *Salmonella, Shigella*, and other *Enterobacteriaceae, Pseudomonas, Moraxella, Helicobacter, Stenotrophomonas, Bdellovibrio*, acetic acid bacteria, *Legionella* etc. Gram-negative bacteria also include, e.g., the cyanobacteria, spirochaetes, green sulfur, and green non-sulfur bacteria. Medically relevant gram-negative cocci include, e.g., *Neisseria gonorrhoeae, Neisseria meningitidis*, and *Moraxella catarrhalis, Haemophilus influenzae*. Medically relevant gram-negative bacilli include a multitude of species. Some of them cause primarily respiratory problems (*Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*). Gram-negative bacteria associated with hospital-acquired infections include, e.g., *Acinetobacter baumannii*, which cause bacteremia, secondary meningitis, and ventilator-associated pneumonia in hospital intensive-care units.

In some embodiments, the composition and the methods as described herein can be used to treat gram-negative bacterial infection. In some embodiments, the bacterial infection is carbapenem-resistant enterobacteriaceae infection, *Klebsiella oxytoca* infection, *Klebsiella pneumoniae* infection, *Campylobacter* infection, extended spectrum enterobacteriaceae (e.g., *E. coli, salmonella, Shigella* and *Yersinia*) infection.

The methods described in the present disclosure are effective for treating bacterial infection in a variety of subjects including humans and animals, such as laboratory animals, e.g., mice, rats, rabbits, or monkeys, or domesticated and farm animals, e.g., cats, dogs, goats, sheep, pigs, cows, horses, and birds, e.g., chickens and turkeys.

Healthcare providers can identify subjects in need of treatment for bacterial infection using their experience and judgment, which can be based on subjective (e.g., based on the healthcare provider's opinion) or objective (e.g., measurable by a test or diagnostic method) information. As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

The present disclosure provides methods of inhibiting or reducing the risk of bacterial infections and for treating bacterial infections. As used herein, the term "reducing the risk" refers to reducing the probability of developing a disorder or condition in a subject, who does not have, but is at risk of, or susceptible to, developing a disorder or condition.

In some embodiments, the genetically engineered microorganisms can be administered to a subject with some other known treatments for bacterial infection. For example, the genetically engineered microorganisms can be used in combination with an antibiotic therapy, such as metronidazole, vancomycin, bacitracin, and/or teicoplatin. In some embodiments, the genetically engineered microorganisms are administered to the subject after the subject have received an antibiotic therapy. In some embodiments, the genetically engineered microorganisms are administered to the subject before the subject has received an antibiotic therapy. In other embodiments, the genetically engineered microorganisms are administered to the subject when the subject is under an antibiotic therapy.

In some embodiments, the genetically engineered microorganisms can be administered to a subject with alkaline phosphatase. These methods involve administering to the subject a composition including the genetically engineered microorganisms and an amount of an alkaline phosphatase effective to increase the number of commensal bacteria in the gastrointestinal tract, wherein alkaline phosphatase decreases the number of pathogenic bacteria in the gastrointestinal tract, or increases the number of commensal bacteria and decreases the number of pathogenic bacteria in the gastrointestinal tract, thereby modulating gastrointestinal tract flora levels in the subject. The alkaline phosphatase composition, and the methods of use is described in WO 2010/025267, which is incorporated by reference in its entirety.

Methods of Treating Dysbiosis

The compositions and the methods as described herein can be used to treat and/or reduce the risk of dysbiosis and its associated diseases.

Dysbiosis is a term for a microbial imbalance or maladaptation on or inside the body. As used herein, the term "intestinal dysbiosis" refers to microbial imbalance in intestines. Dysbiosis is most commonly reported as a condition in the gastrointestinal tract, particularly during small intestinal bacterial overgrowth (SIBO) or small intestinal fungal overgrowth (SIFO). It has been reported to be associated with various diseases, such as periodontal disease, inflammatory bowel disease, chronic fatigue syndrome, obesity, cancer, bacterial vaginosis, and colitis.

The methods described in the present disclosure are effective for treating dysbiosis in a variety of subjects including humans and animals, such as laboratory animals, e.g., mice, rats, rabbits, or monkeys, or domesticated and farm animals, e.g., cats, dogs, goats, sheep, pigs, cows, horses, and birds, e.g., chickens and turkeys.

Healthcare providers can identify subjects in need of treatment for dysbiosis using their experience and judgment, which can be based on subjective (e.g., based on the healthcare provider's opinion) or objective (e.g., measurable by a test or diagnostic method) information. As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

The present disclosure provides methods of inhibiting or reducing the risk of dysbiosis and for treating dysbiosis. As used herein, the term "reducing the risk" refers to reducing the probability of developing a disorder or condition in a subject, who does not have, but is at risk of, or susceptible to, developing a disorder or condition.

In some embodiments, the genetically engineered microorganisms can be administered to a subject with some other known treatments for dysbiosis.

Methods of Administration

The therapeutic methods disclosed herein (including prophylactic treatments) generally include administration of a therapeutically effective amount of a composition comprising the genetically engineered microorganisms to a subject in need thereof. Such treatment will be suitably administered to subjects, particularly humans, suffering from, having, susceptible to, or at risk for a disease, disorder, or symptom of bacterial infection and/or dysbiosis. Determination of those subjects who are "at risk" can be made by any objective or subjective determination by a diagnostic test or opinion of a health care provider.

A subject is effectively treated when a clinically beneficial result ensues. This may mean, for example, a resolution of the symptoms associated with bacterial infection and/or dysbiosis, a decrease in the severity of the symptoms associated with bacterial infection and/or dysbiosis, or a slowing of the progression of symptoms associated with bacterial infection and/or dysbiosis.

The compositions can also include a pharmaceutically acceptable carrier. The term "pharmaceutically acceptable" refers to molecular entities and compositions that do not produce an adverse, allergic or other untoward reaction when administered to a subject. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

Compositions comprising the genetically engineered microorganisms can be administered to a subject through many different routes, e.g., by endoscopy, by enteroscopy, by colonoscopy, by a nasoduodenal catheter, by enema, or by oral administration. In the case of oral administration, the composition can be delivered in a capsule or pill form. In some embodiments, the composition is in a capsule form, e.g., packaged in gelatin capsules.

The present disclosure also provides a food composition comprising the genetically engineered microorganisms. In some embodiments, the food composition comprises carbohydrates such as, but not limited to, starches such as are contained in rice flour, flour, tapioca flour, tapioca starch, and whole wheat flour, modified starches or mixtures thereof.

In some embodiments, the compositions including the genetically engineered microorganisms are in the form of a liquid, and thus can be used as a beverage. In some embodiments, the beverage composition comprising the genetically engineered microorganisms is naturally sweetened. Suitable natural sweeteners include, but are not limited to, sugars and sugar sources such as sucrose, lactose, glucose, fructose, maltose, galactose, corn syrup (including high fructose corn syrup), sugar alcohols, maltodextrins, high maltose corn syrup, starch, glycerin, brown sugar and mixtures thereof.

In some embodiments, the food or beverage compositions include milk or milk-derived product, e.g., yogurt. In some embodiments, a stabilizer may be combined with the milk-derived product. Combining a stabilizer with the milk-derived product may thicken the milk-derived product. In some embodiments, a stabilizer can be combined with the milk-derived product following completion of microorganism culture. The stabilizer can be selected from, as examples, gums, salts, emulsifiers, and their mixtures. Gums can be selected from, as examples, locust bean gum, xanthan gum, guar gum, gum arabic, and carageenan. In some embodiments, salts include, but are not limited to, sodium chloride and potassium chloride.

Dosage

The compositions can be formulated in a unit dosage form, each dosage containing, for example, from about 0.005 mg to about 2000 mg of the genetically engineered microorganisms. The dosage scheduling can be approximately once per week, twice per week, three times per week, or four times per week. In some embodiments, the compositions can be administered to a subject every day, every other day, every three days, every four days, every five days, every six days, or once per week. A person skilled in the art can refine the dosage scheduling as needed.

The phrase "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. When referring to these pre-formulation compositions as homogeneous, the active ingredient is typically dispersed evenly throughout the composition so that the composition can be readily subdivided into equally effective unit dosage forms.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the genetically engineered microorganisms.

Kits

The present disclosure also provides kits of the genetically engineered microorganisms. In some embodiments, the kit includes a sterile container which contains a therapeutic or prophylactic composition having the genetically engineered microorganisms. Such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The kit can also include instructions, e.g., information about the use of the composition for treating a bacterial infection. The kit can further contain precautions; warnings; indications; counter-indications; overdose information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The invention is further described in the following examples, which do not limit the scope of the invention described in the claims.

Materials and Methods

The following materials and methods were used in the following examples.

Microbial Strains, Media, and Growth Conditions

Strains used in this example include *Escherichia coli* strain NEB10β (New England Biolabs. Ipswich, Mass.), *E. coli* strain DH5α (New England Biolabs. Ipswich, Mass.), *E. coli* strain Nissle 1917 and/or *Salmonella enterica* subsp. *Enterica; Serovar Typhimurium* ATCC 29630 (ATCC). Plasmid constructs developed in this work were first transformed by electroporation into *E. coli* NEB10β cells, and then to *E. coli* Nissle (EcN). Oligonucleotides used in this example are listed in Table 1. All media and additional reagents listed in this example were purchased from Sigma Aldrich, St. Louis, Mo., unless otherwise indicated.

The pJPMcH47 and pttrMcH47 plasmids were constructed using standard methods for Gibson Assembly (Gibson, D. G., Young, L., Chuang, R.-Y, Venter, J. C., Hutchison, C. A., and Smith, H. O. (2009) Enzymatic assembly of DNA molecules up to several hundred kilobases. Nat. Methods 6, 343-345.), and the Gibson Assembly Master Mix (New England Biolabs. Ipswich, Mass.). To construct the pJPMcH47 plasmid, a linear version of pBR322 was produced by polymerase chain reaction using primers pBR322FWD and pBR322REV, and select regions of pLJV3 (plasmid that comprises rhaPBAD, CFP, mccF, and mchA genes) and pEX2000 (plasmid that comprises mchXIBCDEF) were amplified using primer sets pLJV3FWD/pLJV3REV and pEX2000FWD/pEX2000REV, respectively. The pttrMcH47 plasmid was constructed by amplification of pJPMcH47 using primers pJPMcH47FWD/pJPMcH47REV and amplification of the ttrRSBCA operon of *S. Typhimurium* using primers SentFWD/SentREV.

TABLE 1

Strains, Plasmids, and Oligonucleotides

| Strains | Relevant characteristics/ sequence (5'-3') | Source or Reference |
|---|---|---|
| *Escherichia coli* Nissle 1917 | | |
| *Salmonella Typhimurium* | *Salmonella enterica* subsp. *enterica* serovar Typhimurium ATCC 29630 | ATCC |
| *Escherichia coli* NEB10β | Δ(ara-leu) 7697 araD139 fhuA ΔlacX74 galK16 galE15 e14-φ80dlacZ ΔM15 recA1 relA1 endA1 nupG rpsL (StrR) rph spoT1 Δ(mrr-hsdRMS-mcrBC) | New England Biolabs |
| *Escherichia coli* DH5α | F-Φ80lacZ ΔM15 Δ(lacZYA-argF) U169 recA1 endA1 hsdR17 (rk-, mK+) phoA supE44 λ-thi-1 gyrA96 relA1 | New England Biolabs |

| Plasmids | | |
|---|---|---|
| pBR322 | pMB1, ApR, TcR | New England Biolabs |
| pLJV3 | pUC57, CFP, mchA, rhaPBAD | synthesized by General Biosystems |
| pJPMcH47 | rhaPBAD driving expression of mchXIB, mchC, mchD, mchE, mchF; J23119 driving expression of mchA | |
| pttrMcH47 | Pttr driving expression of ttrB, ttrC, ttrA, mchXIB, mchC, mchD, mchE, mchF; ttrS and ttrR; J23119 driving expression of mchA; | |
| pEX2000 | pBR322, mchAXIBCDEF | |

TABLE 1-continued

Strains, Plasmids, and Oligonucleotides

| pPP2000 | rhaPBAD driving expression of mchXIB, mchC, mchD, mchE, mchF; J23119 driving expression of mchA, mchS1, mchS4; | |
|---|---|---|

| Oligonucleotides | | |
|---|---|---|
| pBR322FWD | GGATTATTTCTATTTAAAATGAGGCCCT TTCGTCTTCAAGAATTCT (SEQ ID NO: 19) | |
| pBR322REV | GAGATAGCGGTAGCTAACTAGACGTCA GGTGGCACTTTTCG (SEQ ID NO: 20) | |
| pLJV3FWD | TTACCAGACCTCACCCAGACTTCATTA CGACCAGTCTAAAAAGCGCCTG (SEQ ID NO: 21) | |
| pLJV3REV | GAAAAGTGCCACCTGACGTCTAGTTAG CTACCGCTATCTCCAACGTGC (SEQ ID NO: 22) | |
| pEX2000FWD | TTTAGACTGGTCGTAATGAAGTCTGGG TGAGGTCTGGTAAGA (SEQ ID NO: 23) | |
| pEX2000REV | CTTGAAGACGAAAGGGCCTCATTTTAA ATAGAAATAATCCTGTCAACAGTTCTC AACG (SEQ ID NO: 24) | |
| pJPMcH47FWD | AAAAATCGAGCGTATATAACGTCTGGG TGAGGTCTGGTAAGA (SEQ ID NO: 25) | |
| pJPMcH47REV | TCTGTTGGTTTGATCTGGCGGGATGTG ACGATCGTTGACAGC (SEQ ID NO: 26) | |
| SentFWD | TTACCAGACCTCACCCAGACGTTATAT ACGCTCGATTTTTGCCGGC (SEQ ID NO: 27) | |
| SentREV | TGTCAACGATCGTCACATCCCGCCAGA TCAAACCAACAGAA (SEQ ID NO: 28) | |

Solid Media Inhibition Assays

Inhibition assays in solid media were designed and carried out based on the methods as described in Delgado et al. (2005) YojI of *Escherichia coli* functions as a microcin J25 efflux pump. J. Bacteriol. 187, 3465-3470, which is incorporated by reference in its entirety. Briefly, select bacterial strains were grown overnight on LB agar plates, individual colonies were selected and used to inoculate 3 mL of LB broth, and after overnight growth 1 µL of liquid culture was then used to create an agar stab in solid media and incubated at 37° C., either aerobically or anaerobically, for 24 hours. Post incubation, cells were inactivated with chloroform and UV. Molten 3% agar was then added to an overnight culture of susceptible cells to a final concentration of 0.75%, and then 3 mL of the mixture was overlaid on top of the inactivated agar stab plates and allowed to solidify. After incubation of plates in aerobic conditions overnight at 37° C., ImageJ software was utilized to quantify the area corresponding to the inhibition halo.

For solid medium inhibition assays of *S. Typhimurium* and *E. coli* DH5α by EcN pJPMcH47, agar stabs were made in M9 minimal salts supplemented with 0.1 mM $CaCl_2$, 2 mM MgSO$_4$, 0.2 mM 2,2'-dipyridyl, and 0.4% L-rhamnose. For variable L-rhamnose concentration inhibition experiments, culture stabs of EcN pJPMcH47 were made in LB agar supplemented with 0.2 mM 2,2'-dipyridyl and L-rhamnose, ranging from 0.25 µM to 10 mM. All aspects of inhibition assays utilizing plasmid pJPMcH47 were performed in aerobic conditions.

For solid medium inhibition assays of S. Typhimurium by EcN pttrMcH47, culture stabs in LB agar supplemented with 0.2 mM 2,2'-dipyridyl and 1 mM potassium tetrathionate were incubated anaerobically at 37° C. for 24 hours in Oxoid anaerobic jars with anaerobic atmosphere generation bags. Notably, potassium tetrathionate was not added to the LB agar medium until the temperature had reached 50° C., and was prepared immediately before introduction to the media and sterilized by filtration using 0.22 µm filter membrane. Upon removal from the jars, cells were immediately inactivated, overlaid with S. Typhimurium culture in 0.75% agar, and incubated aerobically overnight.

Liquid Media Competition Assays

Competition assays were carried out in triplicate for each experimental condition in a Forma Scientific Model 1025 anaerobic chamber. LB was allowed to equilibrate in anaerobic conditions overnight, prior to initiation of any competition assays. Individual test tubes comprising 3 mL of LB supplemented with final concentration of 0.2 mM 2,2'-dipyridyl, and both 1 mM potassium tetrathionate and 100 µg/mL carbenicillin, as indicated were prepared. Potassium tetrathionate was prepared immediately before inoculation and sterilized by filtration using 0.22 µm filter membrane. Individual colonies of EcN pttrMcH47 and S. Typhimurium and S. Typhimurium pBR322 were selected from LB agar plates, and incubated aerobically overnight at 37° C. in 3 mL of LB, supplemented with 100 µg/mL carbenicillin when relevant. Liquid cultures were then transferred to the anaerobic chamber, and ~10$^5$ cells of each culture were transferred into media for experimental conditions for analysis of relative fitness in competition, based on presence of tetrathionate. Competition assays were set up to compete EcN pttrMcH47 with S. Typhimurium, and EcN McH47 with S. Typhimurium pBR322, in which case 100 µg/mL carbenicillin was supplemented to the media.

Tetrathionate Utilization Assay

Tetrathionate utilization tests were performed by streaking an overnight liquid culture of EcN WT, S. Typhimurium, or EcN pttrMcH47 cells onto modified EMB agar plates, with the exception that the media included just 1 mM potassium tetrathionate. Acidification of the media, and subsequent green sheen, was indicative of tetrathionate reductase activity. Plates were incubated aerobically or anaerobically, as above, for 24 hours at 37° C. At the indicated time points, 200 µL of each competition assay was transferred to a 96-well plate, removed from the anaerobic chamber, immediately serial diluted is phosphate buffered saline (PBS), and then plated onto MacConkey agar plates and incubated aerobically at 37° C. The number of cells of each type (differentiated based on color on MacConkey agar) were measured and calculated in terms of colony forming units (CFU)/mL.

Example 1: Construction and Analysis of Plasmid-Based System for the Inducible Production of Microcin H47

Figure 1A:
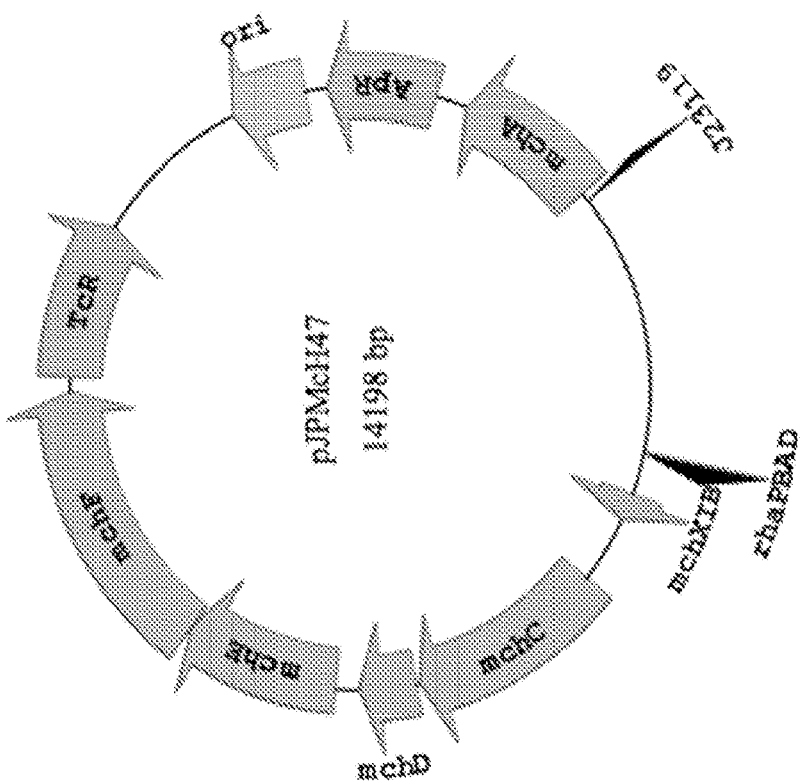
FIG. 1A is a plasmid map for pJPMcH47 that enables L-rhamnose-induced production of microcin H47 (MccH47).
Figure 2A:
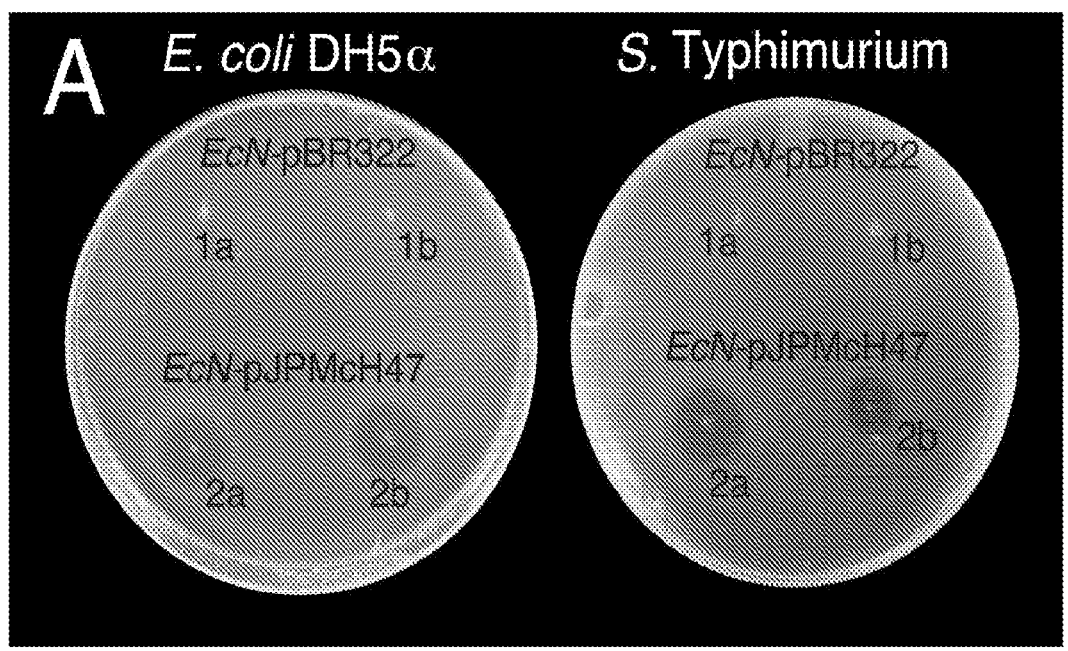
FIG. 2A are representations of plates with pathogenic S. Typhimurium (left) and E. coli DH5α (right) grown as lawns on minimal media supplemented with 22 mM L-rhamnose and 0.2 mM 2,2'-dipyridyl and then challenged by addition of another bacteria to specific positions of the plates; EcN wild-type (herein referred to as EcN-WT) added to spots labeled 1a and 1b and EcN transformed with pJPMcH47 (herein referred to as "EcN-pJPMcH47") added to spots labeled 2a and 2b.
Figure 2B:
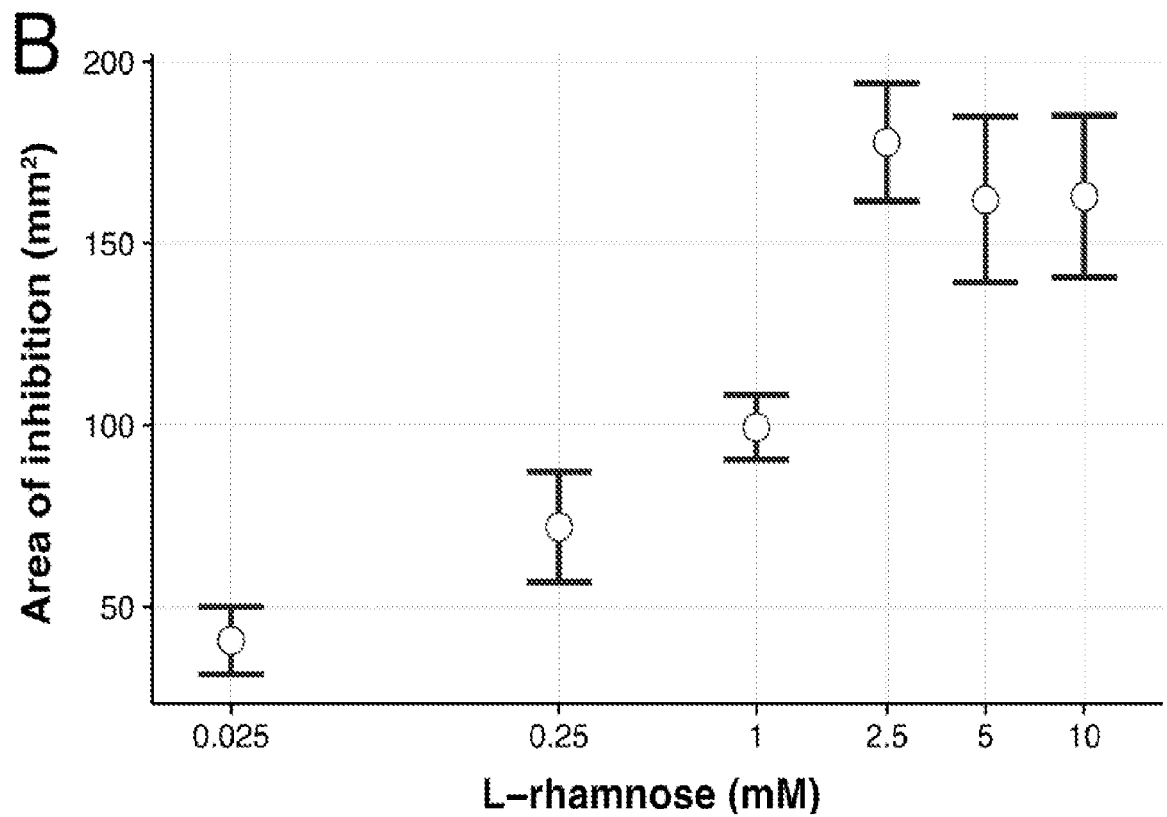
FIG. 2B is a graph depicting area of inhibition in S. Typhimurium lawns grown on LB agar plates supplemented with 0.2 mM 2,2'-dipyridyl and different concentrations of L-rhamnose and then challenged by addition of either EcN-WT or EcN-pJPMcH47 to specific positions of the plates.
Figures 3A, 3B, 3C, 3D:
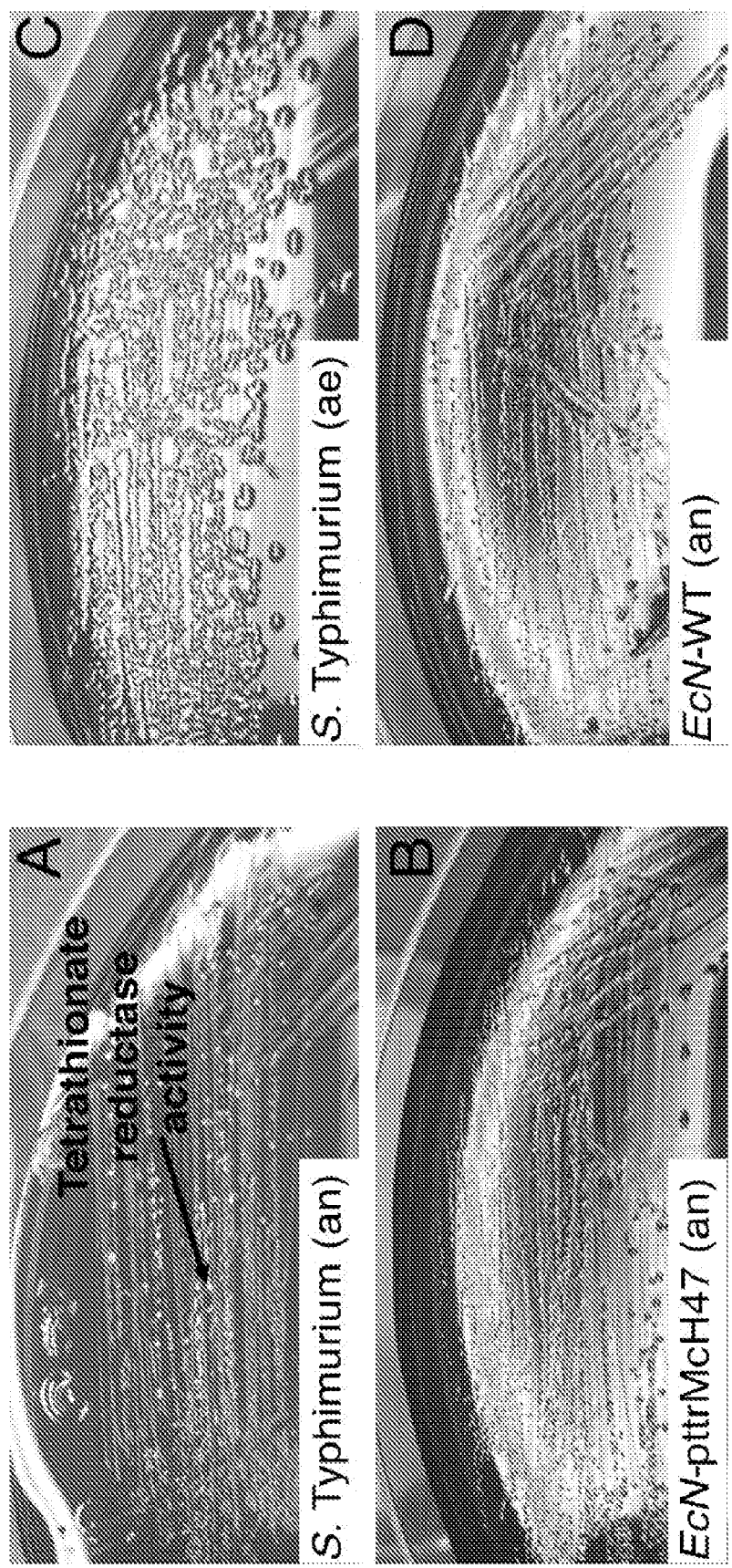
FIGS. 3A-3D are representations of plates with S. Typhimurium, EcN-WT, or EcN transformed with pttrMcH47 (herein referred to as "EcN-pttrMcH47") grown either in anaerobic (an) or aerobic (ae) conditions. The green metallic sheen indicates indirect detection of tetrathionate reductase activity and direct detection of media acidification.

Plasmid pJPMcH47 was developed for the L-rhamnose dependent production of MccH47, and constructed by Gibson Assembly. pJPMcH47 contains all mch genes of E. coli H47 (mchAXIBCDEF), with the mchXIB genes immediately downstream of the rhaPBAD promoter (FIG. 1A). The aim of this design is to specifically regulate production of the MccH47-precursor (MchB), based on L-rhamnose concentration. For the purpose of in vitro assays, E. coli strain NEB10β pJPMcH47 and EcN pJPMcH47 were developed, and then were assessed for the ability of each strain to inhibit Salmonella enterica subsp. Enterica Serovar Typhimurium (hereafter referred to as S. Typhimurium) and E. coli strain DH5α. Inhibition assays were based on the methods as described in Delgado, M. A., Vincent, P. A., Farias, R. N., and Salomón, R. A. (2005) YojI of Escherichia coli functions as a microcin J25 efflux pump. J. Bacteriol. 187, 3465-3470. Inhibition was evaluated visually by measuring a zone of inhibition in susceptible lawns grown on agar plates previously stabbed with a strain carrying pJPMcH47 and inactivated with chloroform and UV. Both EcN pJPMcH47 (FIG. 2A) and E. coli NEB10β pJPMcH47 (data not shown) were capable of inhibiting both S. Typhimurium and E. coli DH5α. Moreover, the level of inhibition was dependent upon L-rhamnose concentration, as evidenced by the positive correlation between L-rhamnose concentration and inhibition area (FIG. 2B). Taken together, these results demonstrate MccH47 as the causative agent in the inhibition of S. Typhimurium. This surprisingly contrasts recent reports, which found MccH47, as produced from EcN WT, unable to inhibit S. Typhimurium (Sassone-Corsi, M., Nuccio, S.-P., Liu, H., Hernandez, D., Vu, C. T., Takahashi, A. A., Edwards, R. A., and Raffatellu, M. (2016) Microcins mediate competition among Enterobacteriaceae in the inflamed gut. Nature 540, 280-283).

Notably, while EcN WT does contain mchXIBCDEF, it lacks mchA (Vassiliadis et al. (2010) Isolation and Characterization of Two Members of the Siderophore-Microcin Family, Microcins M and H47. Antimicrob. Agents Chemother. 54, 288-297.). The mchA gene is a proposed post-translational modification enzyme which is necessary for mature MccH47 antibacterial activity. This difference may explain the lack of inhibition activity by MccH47 from EcN WT against S. Typhimurium. Additionally, while iron-limitation proved essential for maximum inhibition by the engineered strains, EcN WT could not elicit inhibition activity against S. Typhimurium or E. coli DH5α across any iron limiting conditions (rich and minimal media).

Example 2: Construction and Analysis of Plasmid-Based Tetrathionate-Detection System Plasmid pttrMcH47 (FIG. 1B) was developed to confer utilization of tetrathionate capability and tetrathionate dependent production of MccH47, and was constructed by Gibson Assembly. Plasmid pttrMcH47 contains all genes of the ttr operon from S. Typhimurium (ttrRSBCA), and all genes necessary for mature MccH47 to production, immunity, and secretion (mchAXIBCDEF). mchXIB is encoded immediately downstream of ttrA resulting in co-transcription along with ttrBCA from the ttrBCA promoter. EcN pttrMcH47 was then developed by electroporation. Metabolism of tetrathionate were assessed based on the methods as described in Le Minor, L., Chippaux, M., Pichinoty, F., Coynault, C., and Piéchaud, M. Simple methods for the detection of tetrathionate-reductase in liquid cultures and in isolated colonies. Ann. Inst. Pasteur 119, 733-737 (1970), where media acidification due to H$^+$ production during conversion of tetrathionate to thiosulfate in modified eosin methylate blue (EMB) agar results in a characteristic metallic green sheen. Based on a qualitative comparison, S.

Typhimurium and EcN pttrMcH47 both produced a green metallic sheen in anaerobic conditions, indicative of tetrathionate reductase activity, while EcN WT and *S. Typhimurium* in aerobic conditions did not (FIGS. 3A-3D).

Example 3. Analysis of Tetrathionate-Induced Inhibition

Figure 4A:
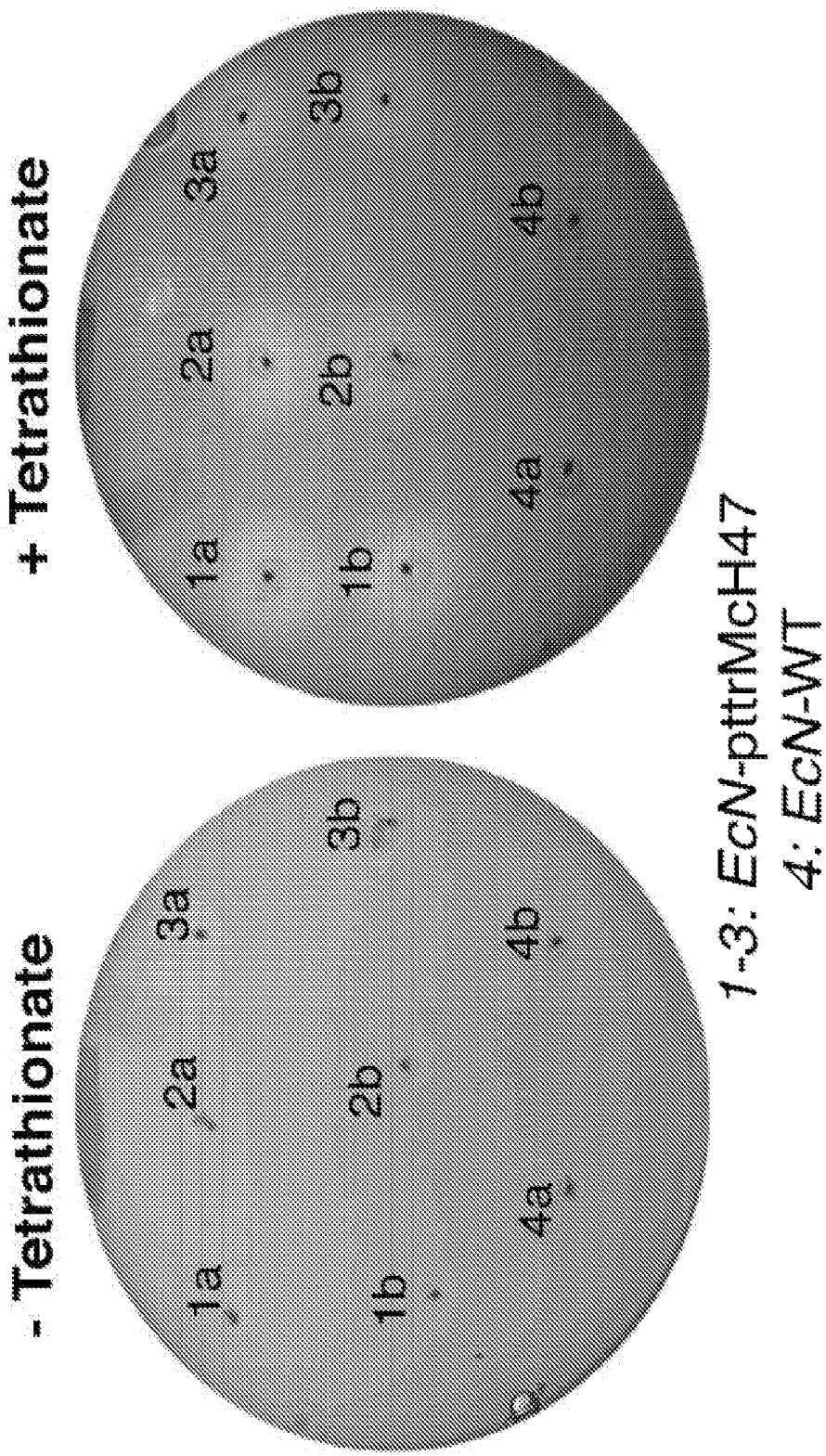
FIG. 4A are representations of plates with pathogenic S. Typhimurium grown as lawns and then challenged by addition of either EcN-WT or EcN-pttrMcH47 to specific positions of the plates; plate shown on right is supplemented with tetrathionate.

After modified EMB media acidification by EcN pttrMcH47, experiments were performed to test the tetrathionate-induced inhibition in vitro. First, solid media inhibition assays were carried out anaerobically in LB agar supplemented with 0.2 mM 2,2'-dipyridyl, with and without 1 mM potassium tetrathionate. In media containing 1 mM potassium tetrathionate, EcN pttrMcH47 was capable of inhibiting *S. Typhimurium* while EcN WT did not (inhibition zone not detected) (FIG. 4A). Unexpectedly, in aerobic conditions, a loss in tetrathionate dependent inhibition was observed, as all culture stabs of EcN pttrMcH47 were capable of inhibiting *S. Typhimurium* while, again, EcN WT showed no inhibition (data not shown). Additionally, supplementation to the media with 0.1% D-glucose fully repressed the inhibition phenotype across all experimental conditions (data not shown).

While static plate assays demonstrate the functional capability of the constructs, these experiments do not account for the effect of competition for growth nutrients. Therefore, competition experiments between EcN pttrMcH47 and either *S. Typhimurium* WT or *S. Typhimurium* pBR322 were performed. Assays were conducted anaerobically, in LB broth supplemented with 0.2 mM 2,2'-dipyridyl, in presence or absence of 1 mM potassium tetrathionate, and supplemented with 100 ug/mL carbenicillin when both strains contained resistance. In experiments to analyze growth rate, it was determined 1 mM of potassium tetrathionate to be a plausible concentration resulting in no significant fitness cost due to tetrathionate (FIGS. 5A-5E). No significant difference in growth dynamics (maximum growth rate) was observed between 0 mM and 1 mM potassium tetrathionate. Maximum growth rate was estimated using the R package grofit and fitting a spline model to the data.

Figure 4B:
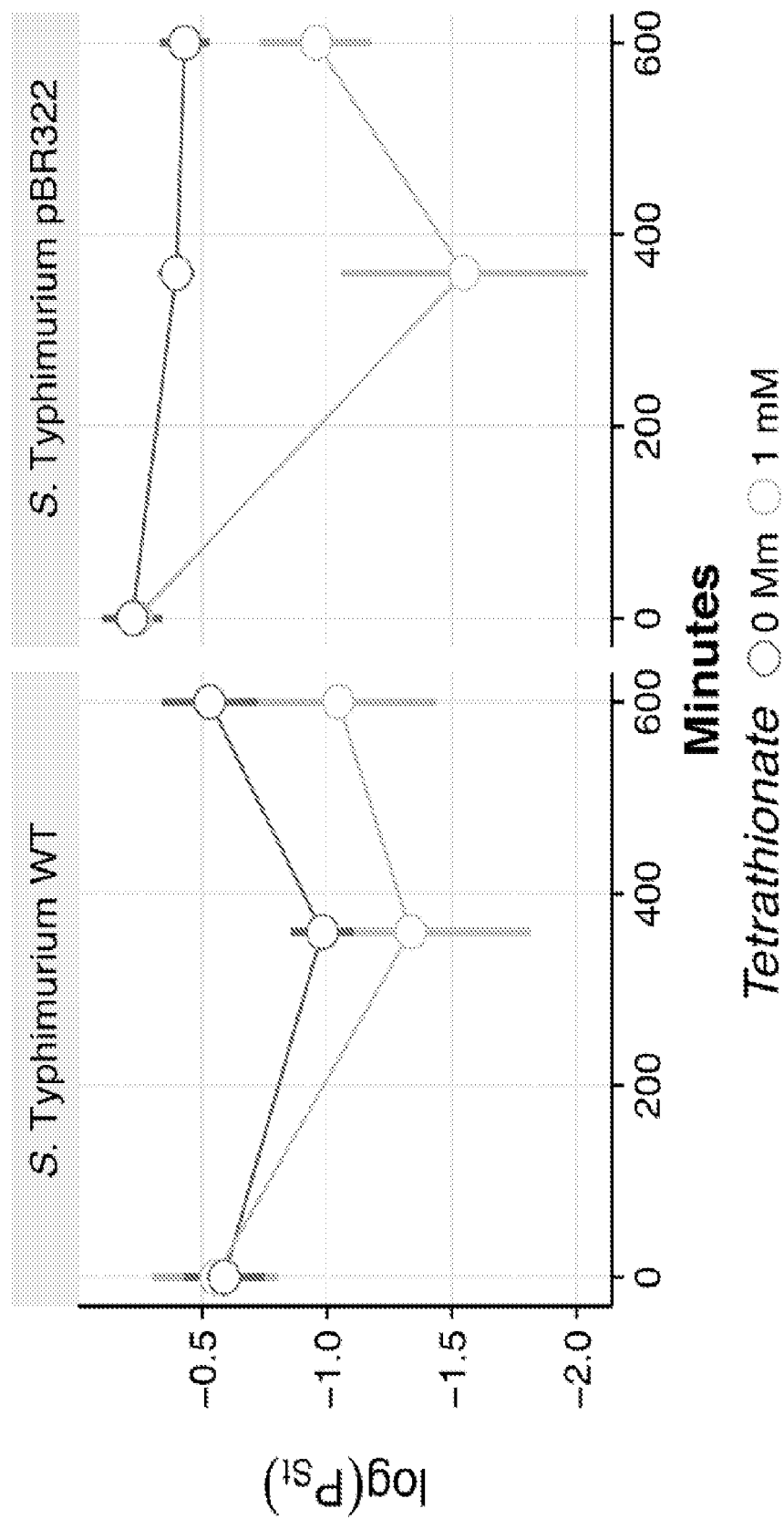
FIG. 4B are graphs depicting results from in vitro ecological competition experiments in which the proportion of S. Typhimurium WT (left) or S. Typhimurium pBR322 (right) is quantified over time.
Figure 4C:
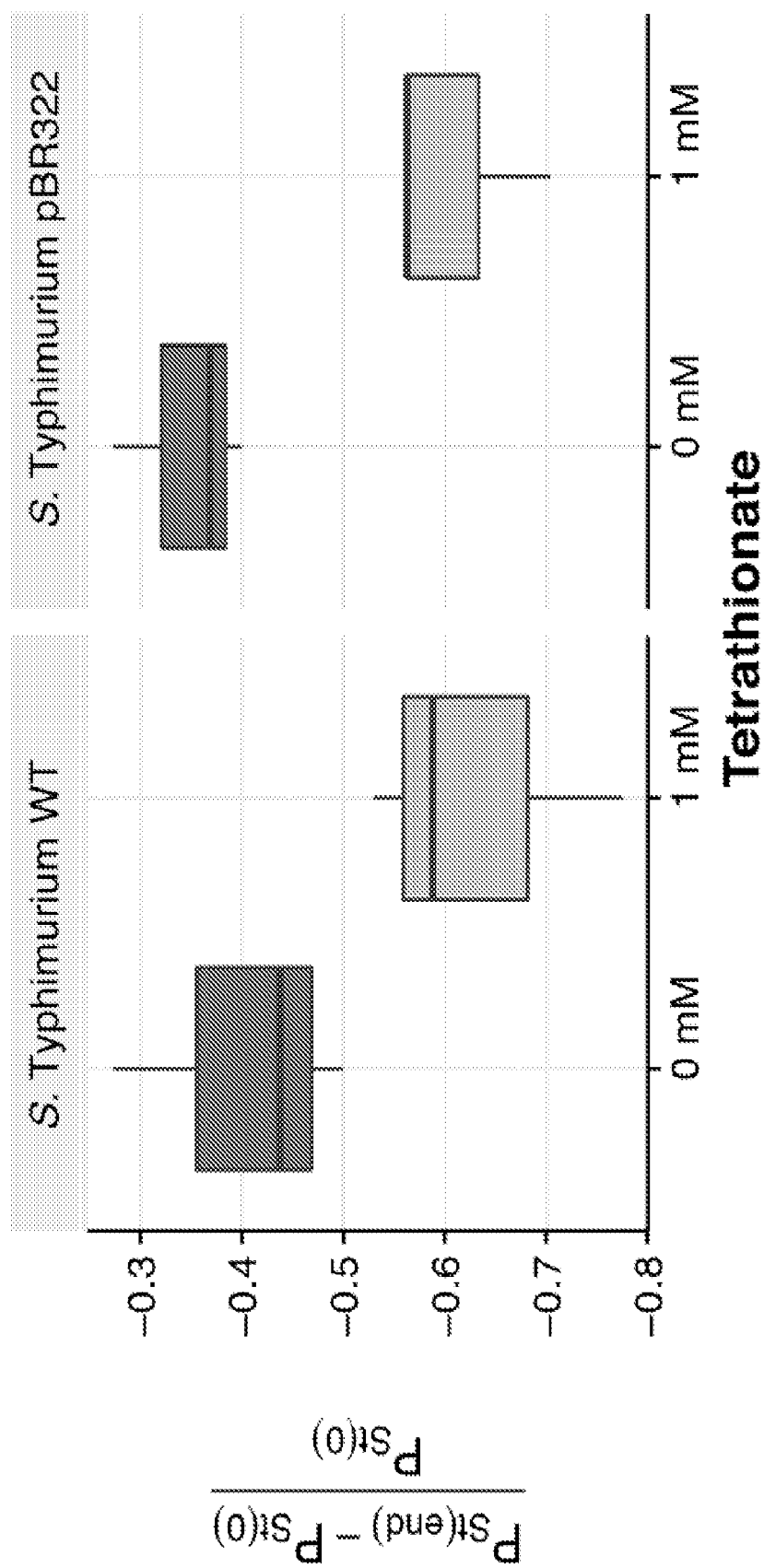
FIG. 4C are graphs depicting fitness of S. Typhimurium wild-type (WT) and S. Typhimurium transformed with pBR322; fitness was estimated from competition experiments performed in presence of 0 or 1 mM potassium tetrathionate.
Figures 5A, 5B, 5C, 5D, 5E:
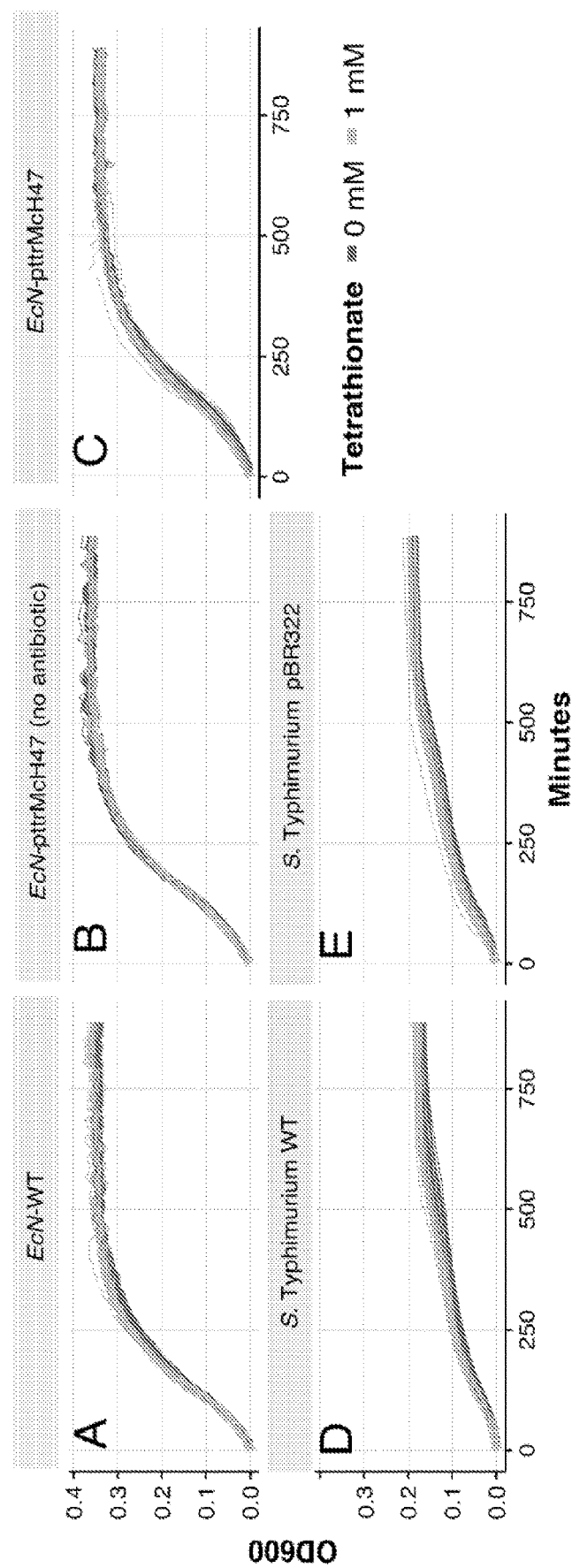
FIG. 5A is a growth curve for E. coli Nissle 1917 (EcN) WT grown under anaerobic conditions on LB media supplemented with 0.2 mM 2,2'-dipyridyl.
FIG. 5B is a growth curve for EcN pttrMcH47 grown under anaerobic conditions on LB media supplemented with 0.2 mM 2,2'-dipyridyl.
FIG. 5C is a growth curve for EcN pttrMcH47 grown under anaerobic conditions on LB media supplemented with 0.2 mM 2,2'-dipyridyl and 100 μg/mL carbenicillin.
FIG. 5D is a growth curve for S. Tyhphimurium WT grown under anaerobic conditions on LB media supplemented with 0.2 mM 2,2'-dipyridyl.
FIG. 5E is a growth curve for S. Tyhphimurium pBR322 grown under anaerobic conditions on LB media supplemented with 0.2 mM 2,2'-dipyridyl and 100 μg/mL carbenicillin.

Competition experiments were initiated with a *S. Typhimurium* (pBR322):EcN pttrMcH47 ratio of approximately 1:1 (FIG. 4B). Bacteria were grown for a total of 10 hours, and 10-fold dilutions were plated onto MacConkey agar for colony enumeration. For both strains, their fitness to the formula below was evaluated, $$W_i = \frac{\Delta P_i}{P_i(0)} = \frac{P_i(end) - P_i(0)}{P_i(0)} \quad (1)$$

wherein $P_i(t)$ is the proportion of strain i at time t (Bucci et al. (2011) The Evolution of Bacteriocin Production in Bacterial Biofilms. Am. Nat. 178, E162E173.); (Nadell et al. (2013) Cutting through the complexity of cell collectives. Proc. R. Soc. B Biol. Sci. 280.). Linear regression analysis was performed and the model $W_{SE}$~1+Tet+Tag was fitted, where Tet and Tag are two "dummy" variables, with Tet indicating absence/presence of tetrathionate and Tag indicating use of *S. Typhimurium* WT or *S. Typhimurium* pBR322. Results of linear regression show a significant decrease in *S. Typhimurium* fitness at 1 mM potassium tetrathionate irrespective of *S. Typhimurium* WT or *S. Typhimurium* pBR322 (p<0.02). This result confirms the ability of EcN pttrMcH47 to suppress *S. Typhimurium* growth beyond what is obtained in direct competition experiments in an environment without the supplementation of tetrathionate (FIG. 4C). The increased competitive advantage of EcN pttrMcH47 over *S. Typhimurium* in an environment supplemented with tetrathionate is particularly important considering recent work which has indicated that tetrathionate in the lumen of the inflamed gut provides a growth advantage for *S. Typhimurium* over the rest of the competing microbiota (Winter et al. (2013) Host-derived nitrate boosts growth of *E. coli* in the inflamed gut. Science 339, 708-711).

Example 4: Construction and Analysis of Plasmid-Based System for the Inducible Production of Microcin H47

Figure 9:
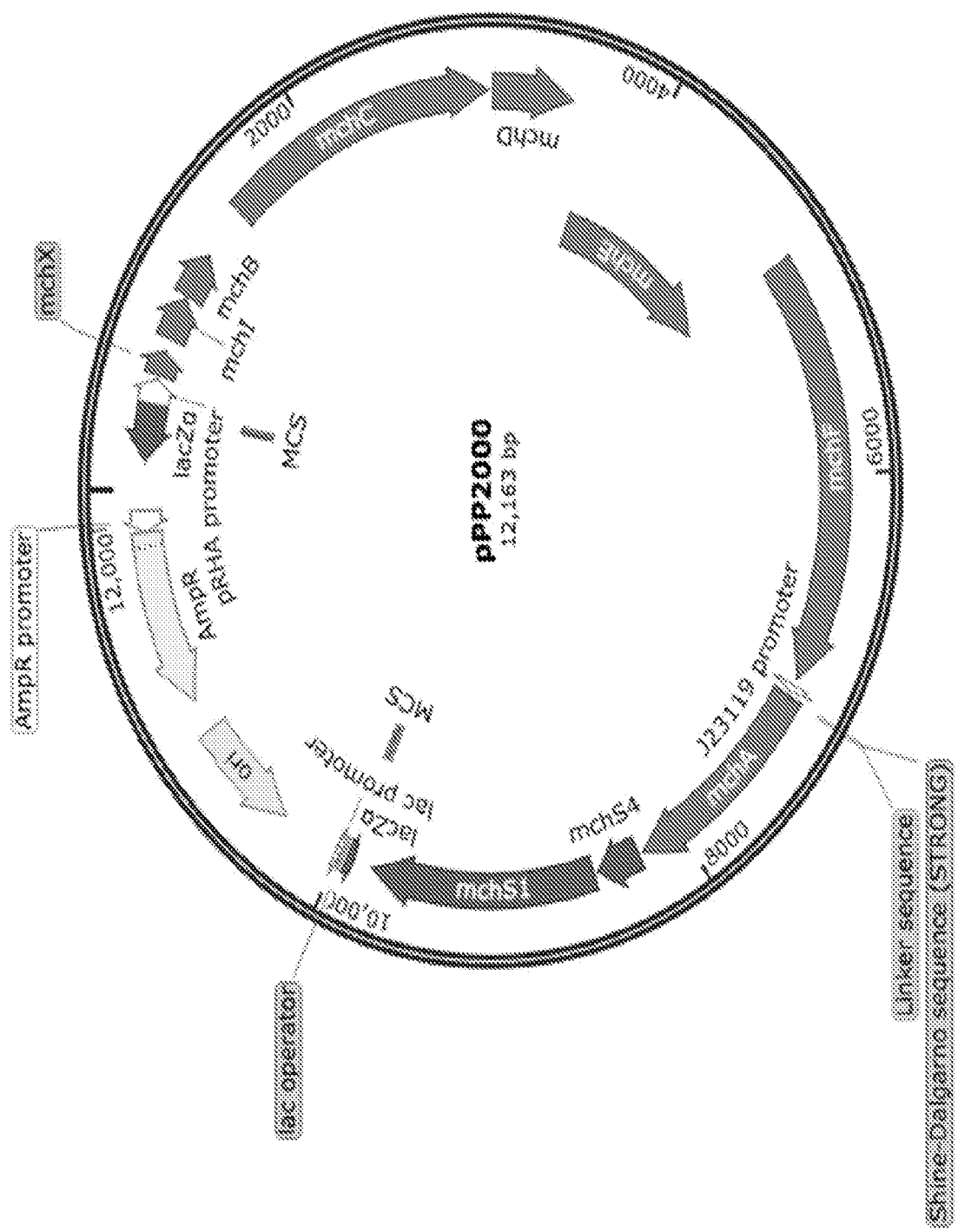
FIG. 9 is a plasmid map for pPP2000 that enables L-rhamnose-induced production of microcin H47 (MccH47).

Plasmid pPP2000 was developed for the L-rhamnose dependent production of MccH47, and constructed by Gibson Assembly. The pPP2000 plasmid contains all mch genes of *E. coli* H47 (mchAXIBCDEFS1S4), with the mchXIB genes immediately downstream of the rhaPBAD promoter and J23119 promoter driving expression of mchA, mchS1, and mchS4 (FIG. 9). The aim of this design is to specifically regulate production of the MccH47-precursor (MchB), based on L-rhamnose concentration. For the purpose of in vitro assays, *E. coli* strain EcN-pPP2000 and EcN-pJPMcH47 were prepared, and then were assessed for the ability of each strain to inhibit *S. Typhimurium*. Inhibition assays were based on the methods as described in Delgado et al. (2005) YojI of *Escherichia coli* functions as a microcin J25 efflux pump. J. Bacteriol. 187,3465-3470.

Figure 10:
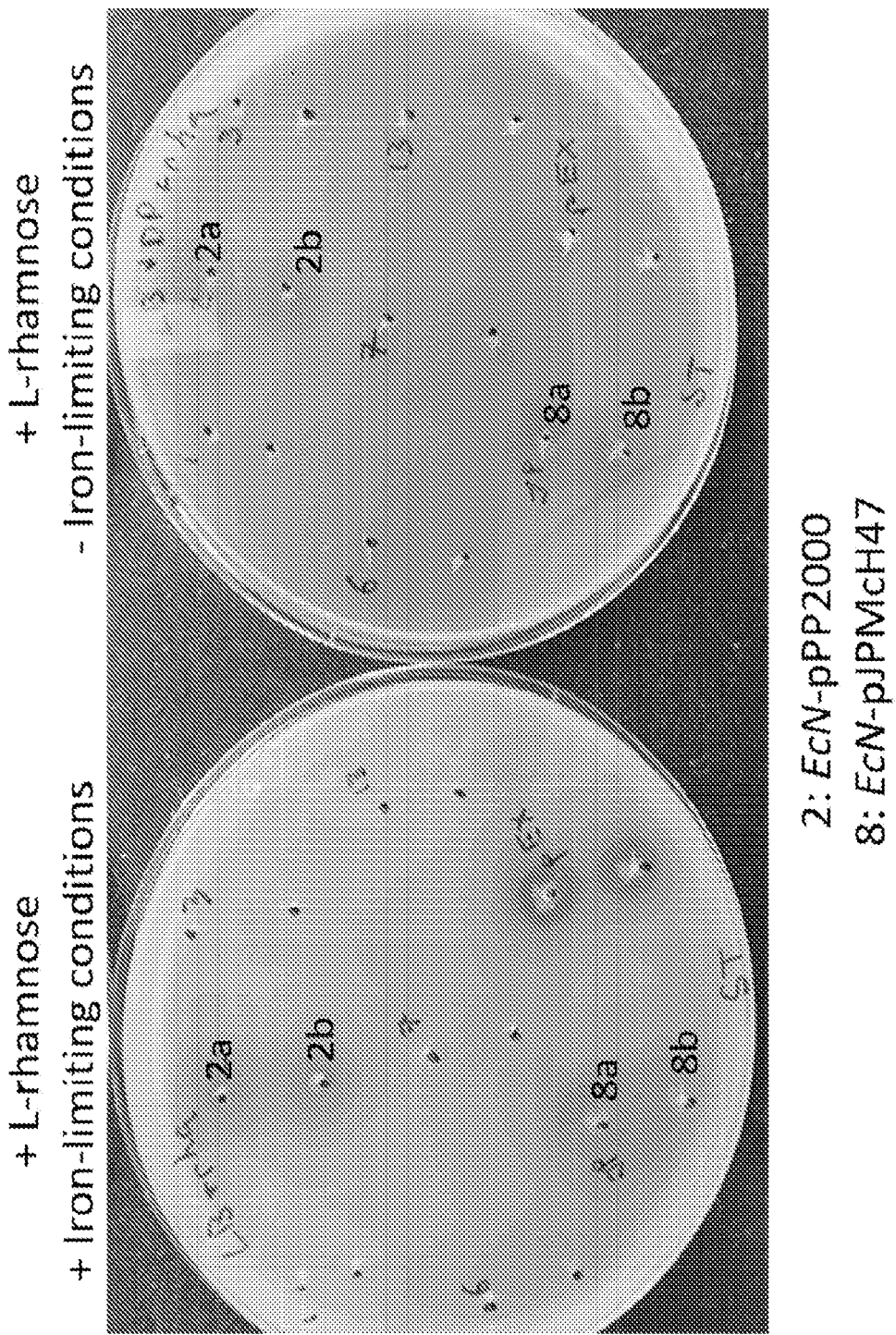
FIG. 10 are representations of plates with S. Typhimurium grown as lawns and then challenged by addition of either EcN-pPP2000 or EcN-pJPMcH47 to specific positions of the plates.

Inhibition was evaluated visually by measuring a zone of inhibition in susceptible lawns grown on agar plates previously stabbed with a strain carrying pJPMcH47 and inactivated with chloroform and UV. Both EcN-pPP2000 and EcN-pJPMcH47 were capable of inhibiting *S. Typhimurium* and the observed inhibition effects were enhanced in iron-limiting conditions (FIG. 10).

Figure 11:
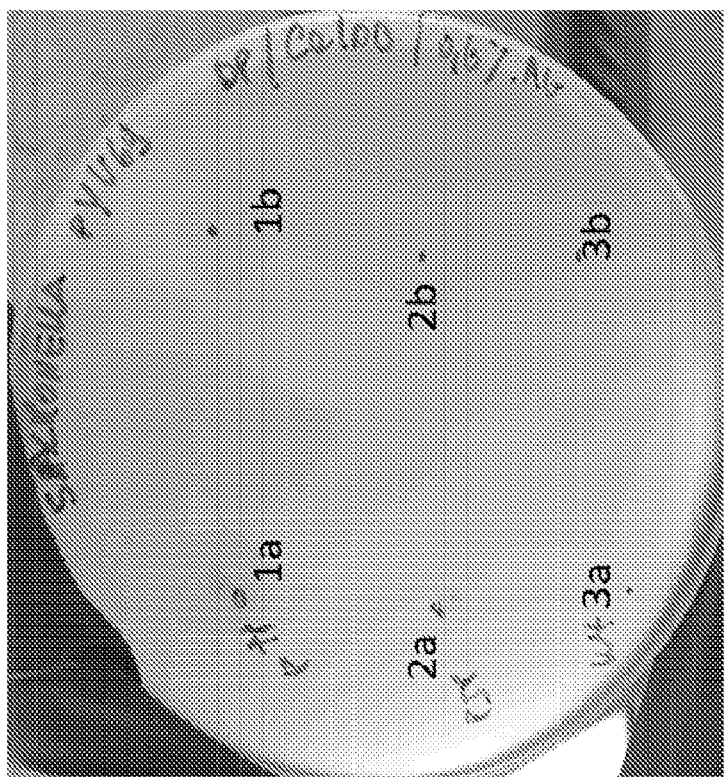
FIG. 11 is a representation of a plate with S. Typhimurium transformed with a low copy vector containing the microcin H47 immunity gene grown as a lawn and then challenged by addition of either EcN-pPP2000 or EcN-pJPMcH47 to specific positions of the plates.

To determine if EcN-pPP2000 is able to inhibit a strain of *S. Typhimurium* that has been transformed with a low copy vector containing the microcin H47 immunity gene, lawns of the aforementioned *S. Typhimurium* were grown and in vitro inhibition assays were performed as previously described. Notably, EcN-pPP2000 was able to inhibit *S. Typhimurium* that has been transformed with a low copy vector containing the microcin H47 immunity gene, while EcN-pJPMcH47 was unable to (FIG. 11). The latter result is consistent with EcN-pPP2000 producing higher levels of MccH47 per bacterial cells compared to MccH47 levels produced by EcN-pJPMcH47.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically engineered microorganism, wherein the microorganism comprises:
    (a) a microcin operon, and
    (b) a controllable promoter for the microcin operon, wherein the microcin operon comprises one or more microcin genes, and the controllable promoter controls a level of expression of the one or more microcin genes, thereby controlling the amount of microcin produced by the genetically engineered microorganism, and wherein either or both of the microcin operon and the controllable promoter are heterologous to the microorganism, and wherein the controllable promoter is a pBAD or Pttr promoter.

2. The genetically engineered microorganism of claim 1, wherein the genetically engineered microorganism is a bacterium.

3. The genetically engineered microorganism of claim 1, wherein the genetically engineered microorganism is *Escherichia coli*.

4. The genetically engineered microorganism of claim 3, wherein the *E. coli* is *E. coli* Nissle 1917 (EcN) or *E. coli* NGF-19.

5. The genetically engineered microorganism of claim 1, wherein the microcin operon comprises one or more Microcin H47 (MccH47) genes.

6. The genetically engineered microorganism of claim 5, wherein the microcin operon comprises mchB, mchC, and mchD.

7. The genetically engineered microorganism of claim 5, wherein the microcin operon comprises mchB, mchC, mchD, mchE, mchF, mchX and mchI.

8. The genetically engineered microorganism of claim 5, wherein the microorganism comprises mchA.

9. The genetically engineered microorganism of claim 1, wherein the microcin operon comprises Microcin M genes or Microcin J25 genes.

10. The genetically engineered microorganism of claim 9, wherein the microcin operon comprises mchS1 and mchS4 genes.

11. The genetically engineered microorganism of claim 1, wherein the controllable promoter is a pBAD promoter.

12. The genetically engineered microorganism of claim 1, wherein the microorganism further comprises a ttrBCA operon.

13. The genetically engineered microorganism of claim 1, wherein the microcin operon and the controllable promoter are in the genome of the microorganism.

14. The genetically engineered microorganism of claim 1, wherein the microcin operon and the controllable promoter are in a vector.

15. A vector comprising:
    (a) a set of microcin genes, and
    (b) a controllable promoter, wherein the controllable promoter is capable of controlling the expression level of at least one microcin gene, wherein the controllable promoter is a pBAD or Pttr promoter.

16. The vector of claim 15, wherein the set of microcin genes comprises one or more Microcin H47 (MccH47) genes.

17. The vector of claim 16, wherein the set of microcin genes comprises mchA, mchB, mchC, and mchD.

18. The vector of claim 16, wherein the set of microcin genes comprises mchA, mchB, mchC, mchD, mchE, mchF, mchX and mchI.

19. The vector of claim 15, wherein the set of microcin genes comprises Microcin M genes or Microcin J25 genes.

20. The vector of claim 19, wherein the set of microcin genes comprises mchS1 and mchS4.

21. The vector of claim 15, wherein the controllable promoter is a pBAD promoter.

22. The vector of claim 15, wherein the vector further comprises an operon comprising one or more of a ttrBCA, a ttrC, and a ttrA.

23. The vector of claim 15, wherein the vector is a plasmid.

24. A method of treating a subject for intestinal dysbiosis or a bacterial infection, the method comprising:
    identifying a subject as having intestinal dysbiosis or a bacterial infection; and
    administering to the subject a therapeutically effective amount of a composition comprising the genetically engineered microorganism of claim 1.

25. The genetically engineered microorganism of claim 1, wherein the controllable promoter is a Pttr promoter.

26. The genetically engineered microorganism of claim 15, wherein the controllable promoter is a Pttr promoter.

27. The method of claim 24, wherein the composition is administered orally.

28. The method of claim 24, wherein the method comprises treating a bacterial infection.

29. The method of claim 28, wherein the bacterial infection is a gram-negative bacterial infection.

30. The method of claim 24, wherein the method comprises treating intestinal dysbiosis.

* * * * *

SEQUENCE LISTING

<160> NUMBER OF SEQ ID NOS: 28

<210> SEQ ID NO 1
<211> LENGTH: 1119
<212> TYPE: DNA
<213> ORGANISM: Escherichia coli
<220> FEATURE:
<221> NAME/KEY: misc_feature
<223> OTHER INFORMATION: mchA gene sequence

<400> SEQUENCE: 1

```
atgcgaaaac gtattctttt tattggccca ccgctgtacg gtttgttata cccattgatt      60
tctctggctc aggcctttcg tgtaatcgga catgatgtag taattagtag tgctggcaaa     120
ttcgcgaata aagcagcaga agctggactg gttgttttttg atgcagttcc aggtttagat    180
tcagaggctg gatatcgcca tcaggaagag ttgaggaaaa aagtaatat tattggtcat      240
ttctcttttt ttagcgatga atggcagat aacctcatcg attttgcagg aaaatggagg      300
ccagatttaa tagtctatcc cccgcttggt ccggcaggcc cattggttgc tgctaaatat    360
agaattcctt cagtgatgct ggctgttgga ttcgcgcata catctgccca tattcagatg    420
ttaaaccgtt ctttaagcaa tgcttacagg cggcatggag tcagcggtcc actatgtgat   480
ttagcatgga ttgatgttgc tcccccaagt atgagcattc ttaaaaatgc tgaagaaccg   540
gttatctcaa tgagatatat tccttataac ggaggtgctg taaaggaaac atggtgggac   600
agggattctg atcgaaaacg tttactcatc agccttggca ctgtaaaacc aatggttgat   660
ggtctggagc tgatttcatg ggttatggat tctgcaaatg aagttgatgc tgatatcatt   720
ttgcaacttg caataaatgc tcgtactgga ttacgaaaac taccatcaaa tgtacgtctg   780
gttgactgga tacctatggg tgtattcctt aatggagctg atggatttat tcatcatggt   840
ggcgcaggta ataccctgac agcgttgtat agtgggatac cacagattgt gtttggcgaa   900
ggtgcagatc gctctgttaa tgcagaaatt gttgcgatgc gtgggtgtgg gattattccg   960
gacaagcatg gactgaccag tgatttggta atcgcctgc tttatgatga ttcactacgc    1020
ttctgttcag atcaggtagc cgctgaaatg gctgaacaac ccagtcctgc agagatcgca   1080
gaggttttga tgagaaaatt aaaaaacaac gggaaataa                            1119
```

<210> SEQ ID NO 2
<211> LENGTH: 1551
<212> TYPE: DNA
<213> ORGANISM: Escherichia coli
<220> FEATURE:
<221> NAME/KEY: misc_feature
<223> OTHER INFORMATION: mchC gene sequence

<400> SEQUENCE: 2

```
atgagtcatc agtgttcact ttctgaactg aatgaaaacc tggtgccttt cactgccagg      60
cagatcaagt cctcattaat ctggtgtgca gaggatgtca gaaatccagg cgagctgcaa    120
aatgcctgca gttatattat cgatcctgac agtacggctt ctgccaaagt gttccatgca    180
gagcgctatg gtggcagtgg tattcagcgt aatggaggtg gtgcacgttg tgggtttgat   240
ggtaactacc aggttaaagg aataggaagt aatccgttgg ttggtgaagg tactgacgaa   300
cgtcattcta tggtgcact cggcgctgtt catgcaatat atgaggcttt gtggggagaa    360
gtactggctc aaatattacc ttatagtgct gtgcgggttc gggcggtttt acttacagat   420
ctctatactg aaaaggcatt tgagcgctcc ggtatgaaat cacgaagagc cctgttggta   480
cgtgagcctg ttgttcgccc ggcgcatttt gaacgggcac catacttcca gtaaaaccg    540
```

```
gagtattcca gtcagttaat tcacgatgcc tgtcgggtta gatctgtgat ccacaagctg    600
ccaggatatc tacctgtacc accggaagaa attgatgctg aagcacgaac tgatccccgg    660
atttattgca ttgagggatt atgtgaactg gcacgtcgtg aggcctggca aatggcattt    720
tgtcgaacac gtttcctgag attgacaact tctccttcta atattgcaat ggatggcaga    780
ttaatggatt taacggact cagttgctcg tttccgggag attccccagc tgattttggg     840
tataaactaa gattagctga actggcaaaa gaaccgatgg tacttatgca agggctgtct    900
gatctctgct tgtatatcgg aaaatatatg tttgaccctg acttcactct gcagcccgt     960 ttgaaggttg aggagatatt tcagaaaact tttcatgaag catgttatta ctgttatcta   1020
gaactgttgg gtattcctgg agaatttata acacaaaaag agatacctga tatattgaaa   1080
caactggtta acagttttgt tgcattactc aataaatact gcgagaaatc acatgcccaa   1140
gatattgtca atcaggatgg ttcaccattg caaaagttgg ttgtgacgct aatccatcat   1200
aggcataatc aaaagcaggc actgaatagt agcatcaaga atgatgttta tttcaccgtt   1260
gcacaacagt gttttttccca gactatccac tggctgacgc aaggcagtac cagacgtcag   1320
ataaatgctt cattactcct gaaagaaatt gaacatcata ccatgaaaag gctgcaaccc   1380
agggaagagc tgaggaaaga gaatatgtgc gaaaaaattg ccatcctgct ggataatcat   1440
ggcgatgatc cccttttttt acaagaagca atttctgata tgaaaaattt tatgcttaag   1500
ttttccagag atgcatttgg atatcttgaa ccgataagaa acacagtgta a             1551

<210> SEQ ID NO 3
<211> LENGTH: 453
<212> TYPE: DNA
<213> ORGANISM: Escherichia coli
<220> FEATURE:
<221> NAME/KEY: misc_feature
<223> OTHER INFORMATION: mchD gene sequence

<400> SEQUENCE: 3
atgtcttata aagggaaac catcagagga aaagatgaat ggactgttta tgaacagata     60
ggttttgcgg tcagttgtat gctctacaat cgtaattaca gtctgtatcc ggtgttaacc   120
attcaatact ggactgaata tgcgatacag cataatcaga ttaaattcct gtttgattca   180
cgaggttttc cactggcgta tataacctgg gcatatcttg aggctgatac ggaagcgcgc   240
ctgctcaggg atccagaatt caggttgcat ccgtctgaat ggaatgaaga tggaaggatc   300
tggatcctgg atttctgttg taaaccaggc tttggtcgaa aagttattga ctatctcata   360
cagcttcagc catgggggga aggagaagta cgatggttaa gcaggcgaaa gaaaattgtg   420
acatacatcc ctgagcggct gcataaaacg tag                                453

<210> SEQ ID NO 4
<211> LENGTH: 228
<212> TYPE: DNA
<213> ORGANISM: Escherichia coli
<220> FEATURE:
<221> NAME/KEY: misc_feature
<223> OTHER INFORMATION: mchB gene sequence

<400> SEQUENCE: 4
atgcgagaaa taacagaatc acagttaaga tatatttccg gggcgggagg tgcgccagcg     60
acttcagcta atgccgcagg tgctgcagct attgttggag ctctcgccgg aatacctggt    120
ggtccacttg gggttgtagt tggagccgta tctgccggtt tgacaacagc aattggctcg    180
```
accgtgggaa gtggtagtgc cagttcttct gctggtggcg gtagctaa        228

<210> SEQ ID NO 5
<211> LENGTH: 1275
<212> TYPE: DNA
<213> ORGANISM: Escherichia coli
<220> FEATURE:
<221> NAME/KEY: misc_feature
<223> OTHER INFORMATION: mchE gene sequence

<400> SEQUENCE: 5
ttgtttcgtc aggatgcttt agaaaacaga aaatgaagt ggcagggacg ggcaatatta        60
cttcccggaa taccactatg gttaatcatg ctgggaagca ttgtgtttat tacggcattt       120
ctgatgttca ttattgttgg tacctatagc cgccgtgtta atgtcagtgg tgaggtcaca       180
acctggccaa gagctgtcaa tatatattca ggtgtacagg gatttgttgt caggcaattt       240
gttcatgaag ggcagttgat aaaaaaggg gatcctgttt atctgattga catcagtaaa        300
agtacacgta gtggtattgt cactgataat catcggcggg atatagaaaa tcagctggtt       360
cgtgtggaca acattatttc ccgtctggaa gaaagtaaaa aaataacgtt agatacctg        420 gaaaaacaac gtctgcaata cacagatgcg tttcgtcgct catcagatat tatacagcgt       480
gcagaggaag ggataaaaat aatgaaaaac aatatggaga attacagaaa ctatcaggca       540
aaagggctga ttaataaga tcagttaact aaccaggtgg cattatatta tcagcaacaa       600
aacaatcttc tcagcctgag cggacagaac gaacagaatg ccctgcagat aaccactctg       660
gagagtcaga ttcagactca ggctgcagat tttgataacc gtatctacca gatggaactg       720
caacggtacg agttacagaa agaactggtt aacactgatg tggagggcga aattattatc       780
cgggcgttga ctgacgggaa agttgactcc ctgagtgtca ctgtcgggca atggtcaat        840 accggagaca gccttctgca ggttattcct gagaacattg aaaactatta tcttattctc       900
tgggtcccaa atgatgctgt tcctatatt tcggctggtg acaaagtgaa tattcgttat        960
gaagcctttc cggcagaaaa atttgggcag ttctctgcta cggttaaaac tatatccagg      1020
actcctgcgt caacacagga aatgttgacc tataagggtg caccacagaa tacgccgggc      1080
gcctctgttc cctggtataa agtcattgcg atgcctgaaa agcagattat cagatatgac      1140
gaaaaatacc tccctctgga aaatggaatg aaagccgaaa gtacactatt tctggaaaaa      1200
aggcgtattt accagtggat gctttctcct ttctatgaca tgaaacacag tgcaacagga      1260
ccgctcaatg actaa                                                       1275

<210> SEQ ID NO 6
<211> LENGTH: 2097
<212> TYPE: DNA
<213> ORGANISM: Escherichia coli
<220> FEATURE:
<221> NAME/KEY: misc_feature
<223> OTHER INFORMATION: mchF gene sequence

<400> SEQUENCE: 6
atgactaacg ggagtttcag acaaattata aatcagcttg atatgcgctg gcgacgtcgt        60
gttccggtta ttcatcagac ggagaccgct gaatgtggac tggcctgcct ggcaatgata       120
tgcggtcatt ttggtaagaa tattgacctg atatctcttc gccggaagtt taatctctcg       180
gcccgtggag caaaccttgc aggaatcaat ggaatagcgg agcagctggg gatggtcacc       240
cgggctcttt cactggagct ggatgaactt ggtgccctca aatgccgtg tattctccac       300 tgggatttca gtcactttgt cgtgctggtc agcgtaaagc gtaaccgtta tgtactgcat       360

```
gatccggcca gaggcagaag atatctcggt cgggaggaaa tgagccggta ttttacgggc      420
attgcacttg aggtctggcc tggaagtgaa ttcctggcgg aaacccagca gatccgcata      480
agtctccgtt cactgattaa cagtatttac ggtattaaaa gaacactggc gaaaattttc      540
tgtctgtcag ttgtaattga agcaatcaat ctggtaatgc cggtggggac tcagctggtt      600
atggatcatg cgattccggc gggggacaga gggctgctga cgcttatttc tgctggcctg      660
atgttcttta tattgctcag gccgcggtg agtatgctgc gtgcatggtc ctcactggtt       720
atgagcacgc tcatcaatat acagtggcag tcgggtctgt ttaaccatct tctcagactg      780
ccgctggcgt tttttgaacg ccgtaaatta ggtgatatcc agtcgcgttt tggctcccctt     840 gacactttga gggccacctt taccacctgt gtggttgggg caatcatgga cagtattatg      900
gttgtggggg ttttgtgat gatgctgtta tatggaggat atcttacctg gatagtgctc       960
ggttttacca tggtttacgt tcttattcgt ctggtgacat acggctatta ccggcaaata     1020
tcggaagaaa ctcttgtcag gggggcccgg gccagctcct atttatgga aagcctgtat      1080 ggtattgcca cggtaaaaat ccaaggtatg gctgggatcc ggggaacaca ctggcttaac     1140
ctgaaaatag atgcgatcaa ttcaggtatt aagttaacca agatggattt gctcttcggg     1200
gggataaata cttttgttgc cgcctgtgat caggtggcga ttttatggct gggtgcaagc    1260
cttgtgatcg ataatcagat gacaataggg atgtttgtgg catttggttc ttttcgtggg    1320
cagttttcgg atcgggttgc ttcgctgacc agttttcttc ttcaactgag aataatgagt    1380
ctgcataatg agcgcattgc agatattgca ctacatgaaa aggaagaaaa gaaaccggaa    1440
attgaaatcg ttgctgacat gagcccggtt tcactggaaa ccactgattt aagctaccgg    1500
tatgacagcc agtcagcaca ggtattcagt ggtctgaatt tgtctgtggc tccgggagaa    1560
agtgtggcta taactggtgc ctccggtgcc ggaaaaacca cattaatgaa agtattatgt    1620
ggactgtttg aaccagatag tggaaaagta ctggttaatg gcacggatat acgtcaactt    1680 ggaataaaata attatcaccg tatgatagcc tgtgttatgc aggacgaccg gctattttca    1740
ggatcaattc gtgaaaatat ctgtgggttt gcagaagaaa cagacgacga atggatgaca    1800
gaatgtgcca gagcaagtca tattcatgat gtgataatga aaatgccaat ggggtatgaa    1860
acgttaatag gtgaactggg ggaaggtctt tccggcggtc aaaaacagcg tatattcatt    1920
gcccgagctt tataccggaa acctggaata ttatttatgg atgaggctac aagttctctt    1980
gatacagaaa gtgaacgttt cgtgaatgct gccataaaaa aatgaatat cacccgggtg     2040 attattgcac acagagaaac tacgttgaga actgttgaca ggattatttc tatttaa       2097

<210> SEQ ID NO 7
<211> LENGTH: 210
<212> TYPE: DNA
<213> ORGANISM: Escherichia coli
<220> FEATURE:
<221> NAME/KEY: misc_feature
<223> OTHER INFORMATION: mchI gene sequence

<400> SEQUENCE: 7
atgagttata aaaaactgta ccaattgacg gctatattta gtttacctct tactatctta      60 ttggttcac tttcatccct tcggattgtt ggcgaaggga attcttatgt tgacgttttt       120
ctaagcttta taatatttct tggttttatt gagctgattc atgggattcg aaagattttg     180
gtctggtcag gctggaaaaa cggaagttaa                                      210
```

```
<210> SEQ ID NO 8
<211> LENGTH: 120
<212> TYPE: DNA
<213> ORGANISM: Escherichia coli
<220> FEATURE:
<221> NAME/KEY: misc_feature
<223> OTHER INFORMATION: mchX gene sequence

<400> SEQUENCE: 8
atggaatttg ctacaaacag ggttactgta aatgacagtc ggtcagcact gtcatcaact      60
ttgctgttgt cttttgatcat gagcgccact ctactggaat attctttatc gatgacctga    120

<210> SEQ ID NO 9
<211> LENGTH: 1266
<212> TYPE: DNA
<213> ORGANISM: Escherichia coli
<220> FEATURE:
<221> NAME/KEY: misc_feature
<223> OTHER INFORMATION: mchS1 gene sequence

<400> SEQUENCE: 9
atgaaaaact atcttttcca gactcccgaa gatatttgtg tacagttaaa aaaaatgaca      60
catcctgtca caataagaac aacagatatt gctaatttct ggcactatct tgagtcagca    120
actcttccgg tgatcacaaa agcaccact acagaaaatc gggaggttac atttctgtgg     180
cgctcagaga aagcagtgca aggcgtatat cttcgcctga tcgtgttac agataaaaaa     240 gatgtcaaaa aaggactaat gactcatatc ccttcgacag atatctggat gctgacactg    300
gtgttaccag cttcatatcg gggctcatac tcatttatag aaattcccac agatatgaca    360
caaaaagaca tatttcaact aggaagtcgc ttctctccat acccggtaa atctgatcca    420 tttaacaaaa cagcagaaat aaatatacga ggattcggag aatcagtcct ttctcttgat    480
atggctcctg aacaaaagga atgggatgat acttcccata aatgtacagg tattctttca    540
acattacatt cctttgttgc aggatatcaa cgccggattc gtttatattt tccccagaat    600
ccaacatcag tacctcttgg attacttgtg ttacctgatg ctgaaatatg gtttgaccgg    660
atggatatta cccgggcatt agatatggcc attaccactg gtcatattgc gccaatggca    720
attatgggga tagacaatat taatgaatct gatcgtatga atatactggg aggcaataaa    780
gaacttatct ttgatatagc ggaaaatctg ataccccagt tatacagaga ctacccgaat    840
atcgtatggg ctggtcgttc taatactata ctggccggtc agagcctcgg tggagtgaca    900
gcactgatgg cagctatata tgcgtcgaca acatttggta caatcattag ccactcacct    960
tcaatgtggt ggaaccctga ccagggcagc ccgattttgt ttactgagaa tgatatctcc   1020
tgggtaagtg agcagatact ttcagcgcct ccgaaagatg taaatatcca acttggagtc   1080
ggttctttag aaggtacaac cgtctcacat gttcagcggt tgcatcagtc gttaatcgca   1140
gcaggtttgg aaagtaacct cactgtctat gccggtggtc atgattatgc ctggtggcgc   1200
ggagcaatta ttgatgcatt agcaaattat aattgcagga agatatcaga taataacttt   1260
gtgtaa                                                              1266

<210> SEQ ID NO 10
<211> LENGTH: 246
<212> TYPE: DNA
<213> ORGANISM: Escherichia coli
<220> FEATURE:
<221> NAME/KEY: misc_feature
<223> OTHER INFORMATION: mchS4 gene sequence

<400> SEQUENCE: 10
```

| | | | | |
|---|---|---|---|---|
| atgaattgtg | ataataatca | cagaaatgaa | gaattcattg | ttacctttga taaaggcaac | 60 |
| aagcaagaca | attcaagacg | aaaacacgat | aattttccta | tagaggtaga atcctccgta | 120 |
| gagctggaga | cacactgtat | cacaaataat | aagtcggctt | ccggtatagt aacacatgac | 180 |
| tatgatccg | attatatttg | tggttgtggt | gaaattatgt | gtcctggttg cggtcatgac | 240 |
| ctataa | | | | | 246 |

<210> SEQ ID NO 11
<211> LENGTH: 3063
<212> TYPE: DNA
<213> ORGANISM: Escherichia coli
<220> FEATURE:
<221> NAME/KEY: misc_feature
<223> OTHER INFORMATION: ttrA gene sequence

<400> SEQUENCE: 11

| | | | | |
|---|---|---|---|---|
| atggctaatt | taacccgtcg | tcagtggcta | aaagtcggtc | tcgccgtcgg tgggatggtc | 60 |
| acttttggtc | tgagctaccg | tgatgtgccg | aaacgcgcaa | ttgatggcct gttaaacggg | 120 |
| acgtccggca | aggtaacgcg | cgaccgcatc | tttggcaatg | cgttaattcc ggaggcgcag | 180 |
| gcgcaaacac | actggcagca | aaatccacaa | caaaccatcg | ccatgacgca atgcttcggc | 240 |
| tgttggacac | agtgcggtat | ccgcgcccgg | gttaatgccg | atggcaaagt gatacgcatc | 300 |
| gccggcaatc | cctatcaccc | cttgtcgcag | gaacacccga | ttgactcgtc cgtccctttt | 360 |
| agcgaagcca | tggagcaact | ggcgggagaa | agcggtcttg | acgcccgctc aaccgcctgc | 420 |
| gcgcgcggcg | ccacgctgct | ggaaagcctg | tacagtccgc | tacgactgct tgaaccgatg | 480 |
| aaacgcgtgg | gtaaacgcgg | cgaagggaaa | tggcagcgca | tcagctttga gcaacttatt | 540 |
| gaagaagtcg | tggaaggcgg | cgatctgttt | ggcgaaggtc | atgtggacgg actgcgcgct | 600 |
| attcatgcgc | cggatacgcc | aattgacgca | agcaccccca | gtttcgggcc caaaaccaat | 660 |
| cagttactgg | tcacgaatac | cagcgacgaa | ggccgcgatg | cgtttctgcg tcgttttgcg | 720 |
| ctaaatagct | tcggcagcaa | gaatttcggc | gcgcatggcg | cctactgtgg actggcttac | 780 |
| cgggccggct | ccggggcatt | gatgggcgat | ctggataaaa | acccgcatgt caaacccgac | 840 |
| tgggaaaacg | tggagtttgc | gctctttatg | ggcacctccc | cggcacagtc cggcaatccg | 900 |
| tttaaacgcc | aggcacgtca | gttggcgagc | gcccgactgc | gtgagaattt tcaatacgtc | 960 |
| gtggtcgccc | cgccctccc | cttatcaacg | gtgctcgccg | atcctcgcgg tcgctggcaa | 1020 |
| ccggtcatgc | ccggcagtga | ttcggcgctg | caatgggga | tgatccgctg gatcatggat | 1080 |
| aatcaacgtt | ataatgctga | ttatctggcg | attcccggcg | tacaggcgat gcagcaggcc | 1140 |
| ggcgagcaaa | gttggaccaa | cgccacgcac | ctggtcattg | cggatgagct gccgacgctt | 1200 |
| gccggacaac | acctgacgct | cgccatctt | acgcccgatg | cgaagagac ccctgtcgta | 1260 |
| ctgaataccg | acggcgagtt | ggtcgatgcg | tccacttgcc | gacaggcacg gcttttcgtg | 1320 |
| acgcagtacg | ttacgctcgc | cgacggccaa | cgggtcacgg | tgaagagcgg gttgcaacgc | 1380 |
| ctgaaagagg | cggcagaaaa | gctctcgttg | gcgcaataca | gcgaacagtg cggcgtgccg | 1440 |
| gaagcgcaaa | ttatcgcgct | ggcggaaacc | tttaccagtc | acggacgtaa agctgcggtc | 1500 |
| atcagtcacg | gcggcatgat | ggccggcaat | gggttttata | cgcctggtc ggtcatgatg | 1560 |
| cttaacgcgc | tgatcggcaa | cctcagcttg | tccggcggcg | tctttgtcgg cggcggcaaa | 1620 |
| ttcaacggcg | ttagcgacgg | cccccgctac | aacatgaaca | gttttgccgg aaaagtgaaa | 1680 |
| ccgtccgggt | taagtattgc | ccgtagcaaa | accgcttatg | aagcatcgga agaataccgc | 1740 |

```
gacaaaattg ccggtgggca atcccttat ccagccaaag cgccgtggta tcccttttgtg    1800 gcaggccagc ttaccgaact gttgacctcc gcgctcgaag gctatcctta tccgcttaaa    1860
gcctggattt ccaatatgag caacccgttt tacggtgttc ccggtctacg cgccgtggcg    1920
gaagaaaaac taaaagaccc tcgccgactg ccgctcttta tcgcgattga cgcctttatg    1980
aatgaaacga cggcgctggc ggattacatt gtgccggata cgcacaattt tgagagctgg    2040
ggctttacgg cgccctgggg cggcgtagcc agtaaagcca ctaccgcccg ctggccggtt    2100 gtcgccccg ccactcaccg cacggcggac gggcaacctg tctcaatgga agcattttgt    2160
attgcggtag caaaacggct ccatctgccc ggcttcggcg accgggcgat aaccgatccg    2220 caggcaata cttttccact gaaccgggcg gaagacttct atctgcgcgt agccgctaat    2280
atcgccttta tgggcaagac gccggtcgcg ctggcaaatc aggaagatat ttcgcttacc    2340
ggcgtcagcc gcattctgcc agcaattcag cacacgctta agctgatga ggtcggtcgc    2400 gtggcgttta tctactcgcg tggcggccgg tttgcgcccg aggatagcgg ctatacggag    2460
caacggttag gtaacgcgtg gaaaaaaccc ttacagatct ggaatgcaga tgtcgccgcc    2520
caccgtcacg ccatcaccgg ggagcgcttc agcggttgcc cggtctggta tccgcgcgt    2580 ttgtcagatg gtcgtgcgat tgacgaccag tttcccattg gcaatggcc gctgaaactg    2640 atttcattta aatcaaatac catgtccagc tcaacagccg tcatcccgcg cttacaccat    2700
gtgaagccag caaacctggt ggcgctgaat ccgcaagacg gcgagcgtta tggactgcaa    2760
catggcgatc gggtacggat cattacgccg ggcggtcagg tcgtggcgca aatcagtttg    2820
ttaaatggcg tgatgccagg cgtcatcgcc atcgaacacg gatatggcca ccgcgagatg    2880
ggcgcaacgc agcactctct ggatggcgtg cctatgccgt atgatccaca aatcagggca    2940
ggcataaatc ttaacgatct gggctttgcc gatccgacaa gaaccattac caacacctgg    3000
ctcgactggg tttctggcgc ggcagtacgt caggggctgc cggcaaaaat cgagcgtata    3060
taa                                                                 3063
```

<210> SEQ ID NO 12
<211> LENGTH: 753
<212> TYPE: DNA
<213> ORGANISM: Salmonella enterica
<220> FEATURE:
<221> NAME/KEY: misc_feature
<223> OTHER INFORMATION: ttrB gene sequence

<400> SEQUENCE: 12

```
atgtggacgg gagtcaatat ggacagcagt aaacggcaat ttctccagca gcttggcgtc     60
ctgaccgctg gcgcctcgct ggttccgctg gctgaagcga aatttccttt ttcgccggag    120
cggcatgaag gctctccccg acaccgttac gccatgctta tcgatctgcg gcgttgtatc    180
ggctgtcagt cctgtaccgt aagttgcact attgaaaacc aaacgccgca aggcgcgttt    240
cgtacgacgg tgaaccaata ccaggtccag cgtgaaggta gtcaggaagt cacgaatgtg    300
ctgttgccgc gtctgtgcaa ccattgcgat aaccccccct gtgtgccggt ctgcccggta    360
caagccacct ttcagcggga agatggcatt gtggtggtgg ataacaaacg ctgcgtcggc    420
tgcgcctatt gtgtccaggc gtgtccttac gacgcccgat ttatcaatca tgaaacgcaa    480
actgccgata aatgcacgtt ttgcgtccat cgtctggaag ccggactgtt acccgcttgc    540
gtagagtcct gcgtcggcgg cgcgcgtatt attggcgata tcaaagatcc ccatagccgc    600
atcgccacca tgcttcatca gcatcgcgac gctatcaagg tattaaagcc ggaaaacggc    660
```

```
acgtcgcccc atgttttcta cctgggtctg gacgacgcct ttgtcacccc attaatgggc    720
cgtgcgcagc ccgcgctttg gcaggaggtc tga                                 753

<210> SEQ ID NO 13
<211> LENGTH: 1023
<212> TYPE: DNA
<213> ORGANISM: Salmonella enterica
<220> FEATURE:
<221> NAME/KEY: misc_feature
<223> OTHER INFORMATION: ttrC gene sequence

<400> SEQUENCE: 13
atgacgcatt cactcatcat tgaagaagtg ctggctcacc cgcaggacat tagctggctg     60
ccgtgggcgg tacaatattt cttttttatt ggcattgccg cctgcgccgc actgtttgcc    120
tgttatcttc actggcggaa aaagacgcc gcaacagaag aaaatcgggc attactgatt     180
gccattacct gtgcgattac cgcaccgctg gcgctgacgg cggatctgca ccagaccgcc    240
cgcgtctggc atttctatgc ctggccgacg ccctggtcgt ggatgccctg gggagcgtta    300
ttcctgccgc tgtttaccgg atttctcgct ctgtggttcc tggcgcagca gattaaacga    360
ttattcaata aaagttacaa cgtcactaaa tggttggcgt tagccagcgc gctttgcgcg    420
gtgggcctgt tgatttatac cggccgcgaa gtctccgttg tgctggcgcg cccaatctgg    480
tttagctacg ccttccccgt ggcgatgttt cttagcgcct acaggcatt cttcgcgctg     540 atgattgtcg ccgcccgaca cgactcggta aggctgccaa aaatattgtg gggacaaatc    600
tggacgctgg cggcgctggg gctggttgtg gccatgtggg ttagcggcga tacgctttcc    660
ggcacggcaa tccgtcagtg gattaccgtc gccctgtcag ccaaatatta cgctgtcggc    720
tgggtagcgc tgtgggtatg cacactgctg ttctgtagcc tggcgctacg ccatccgtta    780
tcacagctaa gacgcgtcct gctggttctc agcgcgctgg cgctatgttg gctgatgcgc    840
tggacattgt tgattcaggt acaaaccgtc cccaagttca acgcgcaatt taacccttac    900
tcgttaccag gcggaacgga tggctggctg gctattctcg gcaccttcgg cctgtggata    960
gcgctactga ttattattcg tgaaacgctg aacggactca ccaggagatt acaacatggc   1020
taa                                                                 1023

<210> SEQ ID NO 14
<211> LENGTH: 1779
<212> TYPE: DNA
<213> ORGANISM: Salmonella enterica
<220> FEATURE:
<221> NAME/KEY: misc_feature
<223> OTHER INFORMATION: ttrS gene sequence

<400> SEQUENCE: 14
gtgagaggta aaaccgtaag gcgcctggcg gtgttggcgg cagtagggct actttgtcat     60
ggcgcgtggg cagggacgtg gaatatcggt attttggcca tgcgcggcga ggcgtctacg    120
cgtagccact ggcaaccgtt ggcaaagaca ttaagccaac agcttccagg cgaaaccttt    180
cacatccagc cgctggatct gcatcaaatg caggaggccg ttaaccaggg aaccgtgcag    240
tttgtgataa ccaacccggc gcaatttgtc caactgaaca gccatgcgcc gctgcgctgg    300
ttagcttccc tgcgctccac gcgcgatggg aaagcggtga gtaatgttat ggcagcgtg     360 attttgaccc ggcgcgatag cggcatcacc acggcgcatg atctcatcgg taagaccgtc    420
ggcgcgattg atgctcaggc gtttggcggc tatttattag gctataaagc gctcagcgac    480
```

```
gcgggcttac gcccggagcg cgattttcat ctccgttttta ccggatttcc tggcgatgcc      540
ttagtctata tgctgcgcga aaaagcggtg caggcggcaa ttgtgccagt gtgcctgtta      600
gaaaatatgg atcaggaagg attgattaat aaaaaggact ttatcgcgct gctttcccga      660
ccgacgcccc tgccttgctt aaccagtacg ccgttatatc ctgactggtc gttcgcggcg      720
ctacctgcgg taagcgatgc gctggcggat cgcgtaacgc gagcgctatt caacgcgccc      780
gccgccgcgt catttcactg gggcgcgcct gcgtccacca gtcaggtgga agccttgctg      840
cgtgatgttc gtcagcaccc tcagcagcgt cgactgtggc tggatgtcaa aagttggtta      900
atccagcacc agctaatggt cggcggcgtg attctggcgt tcttgttgct cacgctcaat      960
tatatttggg tcatgctgct ggtgcgtcga cgtggaaagc aactggaacg taatagcgta     1020
gttcttcatc agcatgagcg ggcgctggaa accgcccggc aaatgagcgt gttgggtgaa     1080
atgacctccg ggtttgccca tgagcttaat cagccgcttt ccgcgattcg acattatgcc     1140
caggggtgcc tgattcgact gcgcgctgca gatgaacagc atcccttgct gccggcgctg     1200
gagcagattg accagcaggc gcaacgcggt gcggatactc tgcgtaacct gcgtcactgg     1260
gtcagccagg cgcagggcaa cccggtgcta accgaagcgt ggaaggccat agccattcgc     1320
gaggcgattg atcatgtctg gcaattgttg cgtatggcgc aacagtttcc gacagtgact     1380
ctgcataccg aggttagcgc tgcgctgcgc gtaacgctgc cgtcagtgct gctggaacag     1440
gtgctggcga atatcattct taatgcggct caggcgggcg ccacccattt atggatcgtt     1500
gctgaacgca ctgaaaacgg catcagtatt gttttacagg ataacgccgg gggaatcgat     1560
gaggcgctat tacgtcaggc gtttcagccg tttatgacca cccgtaaaga ggggatgggc     1620
ttagggctgg cgatttgcca gcggctggtg cggtatgggc ggggcgatat cagcatcagg     1680
aaccagaccg cgccggacgg tctgtcggga acggtggtta cgatacattt cttacatgaa     1740
aatgggggca gggatggcga caattcatct actggatga                            1779

<210> SEQ ID NO 15
<211> LENGTH: 639
<212> TYPE: DNA
<213> ORGANISM: Salmonella enterica
<220> FEATURE:
<221> NAME/KEY: misc_feature
<223> OTHER INFORMATION: ttrR gene sequence

<400> SEQUENCE: 15
atgaaaatgg gggcagggat ggcgacaatt catctactgg atgatgatac ggcggtcact       60
aacgcgtgcg cgttttttact ggaaagtctg ggatatgacg taaatgctg gacgcagggg      120 gcggattttt tggcgcaggc cagtctgtat caggccgggg tcgtattact ggatatgcga      180
atgccggtac tggatgggca gggcgttcat gatgcgttgc gccagtgcgg aagtaccctg      240
gcggttgttt ttcttaccgg gcatggcgat gtaccgatgg ccgtggagca gatgaaacgc      300
ggcgccgtcg attttctgca aaaccggta tcggtaaaac cgctacaggc ggcgctggag      360
cgtgcgctga cggtttcatc ggcagcgtg gcgcgtcgtg agattatact gtgttaccag      420
cagttgacgc cgaaagagcg tgagctggcc agcctggtgg caaaaggatt tatgaaccgt      480
gaaattgcgg aagcgatgaa tatcgcgtg cgtaccgtag aggtgcaccg cgccagagtc      540
atggaaaaaa tgcaggccgg tagcctggcg gaactgatta ggcgtttcga aaaatggcc      600 tcgccagaga ccagaatacg aacaacgtat gagccatga                            639

<210> SEQ ID NO 16
```

```
<211> LENGTH: 122
<212> TYPE: DNA
<213> ORGANISM: Escherichia coli
<220> FEATURE:
<221> NAME/KEY: misc_feature
<223> OTHER INFORMATION: pBAD promoter sequence

<400> SEQUENCE: 16
ccacaattca gcaaattgtg aacatcatca cgttcatctt tccctggttg ccaatggccc      60
attttcctgt cagtaacgag aaggtcgcgt attcaggcgc ttttttagact ggtcgtaatg    120 aa                                                                   122

<210> SEQ ID NO 17
<211> LENGTH: 163
<212> TYPE: DNA
<213> ORGANISM: Salmonella enterica
<220> FEATURE:
<221> NAME/KEY: misc_feature
<223> OTHER INFORMATION: Pttr promoter sequence

<400> SEQUENCE: 17
cccaatatcc ctgtcaatta tgttgtttta gatcaacaac aagccgggta tgtggttaac      60
cacaatagag cgcaccccgc ctcgattttt acactgtaaa tcatcgacat tttttattca    120
ttacacatga accaacatcg tgacaaatgt tcattgttg gca                        163

<210> SEQ ID NO 18
<211> LENGTH: 34
<212> TYPE: DNA
<213> ORGANISM: Artificial Sequence
<220> FEATURE:
<223> OTHER INFORMATION: J23110 promoter sequence

<400> SEQUENCE: 18
ttgacagcta gctcagtcct aggtataatg ctag                                 34

<210> SEQ ID NO 19
<211> LENGTH: 46
<212> TYPE: DNA
<213> ORGANISM: Artificial Sequence
<220> FEATURE:
<223> OTHER INFORMATION: Synthetic primer

<400> SEQUENCE: 19
ggattatttc tatttaaaat gaggcccttt cgtcttcaag aattct                    46

<210> SEQ ID NO 20
<211> LENGTH: 41
<212> TYPE: DNA
<213> ORGANISM: Artificial Sequence
<220> FEATURE:
<223> OTHER INFORMATION: synthetic primer

<400> SEQUENCE: 20
gagatagcgg tagctaacta gacgtcaggt ggcacttttc g                         41

<210> SEQ ID NO 21
<211> LENGTH: 49
<212> TYPE: DNA
<213> ORGANISM: Artificial Sequence
<220> FEATURE:
<223> OTHER INFORMATION: synthetic primer

<400> SEQUENCE: 21
ttaccagacc tcacccagac ttcattacga ccagtctaaa aagcgcctg                 49
```

<210> SEQ ID NO 22
<211> LENGTH: 48
<212> TYPE: DNA
<213> ORGANISM: Artificial Sequence
<220> FEATURE:
<223> OTHER INFORMATION: synthetic primer

<400> SEQUENCE: 22
gaaaagtgcc acctgacgtc tagttagcta ccgctatctc caacgtgc    48

<210> SEQ ID NO 23
<211> LENGTH: 42
<212> TYPE: DNA
<213> ORGANISM: Artificial Sequence
<220> FEATURE:
<223> OTHER INFORMATION: synthetic primer

<400> SEQUENCE: 23
tttagactgg tcgtaatgaa gtctgggtga ggtctggtaa ga    42

<210> SEQ ID NO 24
<211> LENGTH: 58
<212> TYPE: DNA
<213> ORGANISM: Artificial Sequence
<220> FEATURE:
<223> OTHER INFORMATION: synthetic primer

<400> SEQUENCE: 24
cttgaagacg aaagggcctc attttaaata gaataatcc tgtcaacagt tctcaacg    58

<210> SEQ ID NO 25
<211> LENGTH: 42
<212> TYPE: DNA
<213> ORGANISM: Artificial Sequence
<220> FEATURE:
<223> OTHER INFORMATION: synthetic primer

<400> SEQUENCE: 25
aaaaatcgag cgtatataac gtctgggtga ggtctggtaa ga    42

<210> SEQ ID NO 26
<211> LENGTH: 42
<212> TYPE: DNA
<213> ORGANISM: Artificial Sequence
<220> FEATURE:
<223> OTHER INFORMATION: synthetic primer

<400> SEQUENCE: 26
tctgttggtt tgatctggcg ggatgtgacg atcgttgaca gc    42

<210> SEQ ID NO 27
<211> LENGTH: 46
<212> TYPE: DNA
<213> ORGANISM: Artificial Sequence
<220> FEATURE:
<223> OTHER INFORMATION: synthetic primer

<400> SEQUENCE: 27
ttaccagacc tcacccagac gttatatacg ctcgattttt gccggc    46

<210> SEQ ID NO 28
<211> LENGTH: 41
<212> TYPE: DNA
<213> ORGANISM: Artificial Sequence
<220> FEATURE:

```
<223> OTHER INFORMATION: synthetic primer

<400> SEQUENCE: 28
tgtcaacgat cgtcacatcc cgccagatca aaccaacaga a                    41
```